(12) United States Patent
Gulak et al.

(10) Patent No.: US 12,093,939 B2
(45) Date of Patent: Sep. 17, 2024

(54) SYSTEM AND METHODS FOR VALIDATING AND PERFORMING OPERATIONS ON HOMOMORPHICALLY ENCRYPTED DATA

(71) Applicant: LORICA CYBERSECURITY INC., Toronto (CA)

(72) Inventors: Glenn Gulak, Toronto (CA); Alhassan Khedr, Toronto (CA)

(73) Assignee: LORICA CYBERSECURITY INC., Toronto (CA)

( * ) Notice: Subject to any disclaimer, the term of this patent is extended or adjusted under 35 U.S.C. 154(b) by 0 days.

(21) Appl. No.: 16/297,803

(22) Filed: Mar. 11, 2019

(65) Prior Publication Data

US 2019/0205875 A1     Jul. 4, 2019

Related U.S. Application Data

(63) Continuation of application No. 15/468,621, filed on Mar. 24, 2017, now abandoned.
(Continued)

(51) Int. Cl.
    *G16H 10/40*        (2018.01)
    *A61B 5/00*         (2006.01)
    (Continued)

(52) U.S. Cl.
    CPC .......... *G06Q 20/3829* (2013.01); *A61B 5/72* (2013.01); *G06N 20/00* (2019.01); *G06Q 20/382* (2013.01);
    (Continued)

(58) Field of Classification Search
    CPC ......... G06Q 20/3829; G06Q 20/38215; G06Q 20/08; G06Q 2220/00; G06Q 20/382;
    (Continued)

(56) References Cited

U.S. PATENT DOCUMENTS

| | | |
|---|---|---|
| 8,515,058 B1 | 8/2013 | Gentry |
| 8,565,435 B2 | 10/2013 | Gentry et al. |

(Continued)

FOREIGN PATENT DOCUMENTS

| | | |
|---|---|---|
| CN | 104700277 | 6/2015 |
| EP | 2728790 | 7/2014 |

(Continued)

OTHER PUBLICATIONS

Jung Hee Cheon; A Hybrid Scheme of Public-Key Encryption and Somewhat Homomorphic Encryption; IEEE transactions on information forensics and security, May 2015, vol. 10 (5), p. 1052-1063, Article 1052.*

(Continued)

*Primary Examiner* — Ilse I Immanuel

(74) *Attorney, Agent, or Firm* — Heer Law; Christopher D. Heer

(57) ABSTRACT

A system and method of validating and performing operations on homomorphically encrypted data are described herein. The methods include processing a secure financial transaction by receiving a transaction request to complete a financial transaction, with at least a portion of the request encrypted according to a homomorphic encryption scheme, and the transaction request comprising confidential cardholder data including an account number, non-confidential cardholder data, and transaction data, and retrieving one or more sets of encrypted comparison cardholder data encrypted according to a homomorphic encryption scheme. The confidential cardholder data is then compared to each set of the comparison cardholder data using one or more homomorphic operations to determine which set of comparison cardholder data matches the confidential cardholder data and validating the confidential cardholder data. An encrypted indicator is generated indicating authorization or (Continued)

rejection of the request and forwarded to a party seeking authorization to complete the financial transaction.

17 Claims, 15 Drawing Sheets

Related U.S. Application Data

(60) Provisional application No. 62/321,411, filed on Apr. 12, 2016, provisional application No. 62/417,490, filed on Nov. 4, 2016.

(51) Int. Cl.
```
G06N 20/00      (2019.01)
G06Q 20/08      (2012.01)
G06Q 20/38      (2012.01)
G16H 10/60      (2018.01)
H04L 9/00       (2022.01)
H04L 9/30       (2006.01)
H04L 9/40       (2022.01)
```
(52) U.S. Cl.
CPC ....... *G06Q 20/38215* (2013.01); *G16H 10/40* (2018.01); *G16H 10/60* (2018.01); *H04L 9/008* (2013.01); *H04L 9/3093* (2013.01); *H04L 63/0414* (2013.01); *H04L 63/0428* (2013.01); *G06Q 20/08* (2013.01); *G06Q 2220/00* (2013.01)

(58) Field of Classification Search
CPC ........ G16H 10/60; G16H 10/40; H04L 9/008; H04L 63/0428; H04L 9/3093; H04L 63/0414; A61B 5/72
See application file for complete search history.

(56) References Cited

U.S. PATENT DOCUMENTS

| | | | |
|---|---|---|---|
| 8,630,422 | B2 | 1/2014 | Gentry |
| 8,712,915 | B2 * | 4/2014 | Staddon ................. G06Q 30/06 705/400 |
| 2014/0233727 | A1 | 8/2014 | Rohloff et al. |
| 2015/0039912 | A1 | 2/2015 | Payton et al. |
| 2015/0154406 | A1 | 6/2015 | Naehrig et al. |
| 2015/0227930 | A1 | 8/2015 | Quigley et al. |
| 2016/0072800 | A1 * | 3/2016 | Soon-Shiong ......... G16B 50/00 726/7 |
| 2017/0053282 | A1 * | 2/2017 | Olumofin ........... G06Q 20/3224 |
| 2017/0063525 | A1 | 3/2017 | Bacon et al. |
| 2017/0149557 | A1 * | 5/2017 | Bacon ................... H04L 9/3093 |
| 2017/0155628 | A1 * | 6/2017 | Rohloff .................. H04L 63/02 |

FOREIGN PATENT DOCUMENTS

| | | | | |
|---|---|---|---|---|
| EP | 3432146 | A1 * | 1/2019 | ............. G06F 9/466 |
| WO | 2014177581 | | 11/2014 | |
| WO | 2016033510 | | 3/2016 | |

OTHER PUBLICATIONS

"Schönhage-Strassen algorithm." Wikipedia: The Free Encyclopedia. Wikimedia Foundation, Inc. Retrieved from <https://en.wikipedia.org/wiki/Sch%C3%B6nhage%E2%80%93Strassen_algorithm#cite_note-sch.C3.B6nhage-1> on Jul. 23, 2015.
Aguilar-Melchor, Carlos, and Philippe Gaborit. "A lattice-based computationally-efficient private information retrieval protocol." Cryptol. ePrint Arch., Report 446 (2007).
Aguilar-Melchor, Carlos, et al. "Recent advances in homomorphic encryption: A possible future for signal processing in the encrypted domain." Signal Processing Magazine, IEEE 30.2 (2013): 108-117. 10 pages.
Alhassan Khedr, P. Glenn Gulak, Vinod Vaikuntanathan: SHIELD: Scalable Homomorphic Implementation of Encrypted Data-Classifiers. IACR Cryptology ePrint Archive 2014: 838 (2014).
Alperin-Sheriff, Jacob, and Chris Peikert. "Faster bootstrapping with polynomial error." Advances in Cryptology—CRYPTO 2014. Springer Berlin Heidelberg, 2014. 297-314.
Baek, Joonsang, Reihaneh Safavi-Naini, and Willy Susilo. "Public key encryption with keyword search revisited." Computational Science and Its Applications—ICCSA 2008. Springer Berlin Heidelberg, 2008. 1249-1259.
Benaloh, J., Vaikuntanathan, V. Homomorphic Encryption: What, How, and Why. people.csail.mit.edu/vinodv/Homomorphic-TECHFEST-Final.ppsx.
Boneh, Dan, et al. "Private database queries using somewhat homomorphic encryption." Applied Cryptography and Network Security. Springer Berlin Heidelberg, 2013.; 24 pages.
Boneh, Dan, et al. "Public key encryption with keyword search." Advances in Cryptology—Eurocrypt 2004. Springer Berlin Heidelberg, 2004.
Bost, Raphael, et al. Machine learning classification over encrypted data. Cryptology ePrint Archive, Report 2014/331, 2014. http://eprint.iacr.org, 2014. 34 pages.
Brakerski, Z., Gentry, C., Vaikuntanathan, V.: Fully homomorphic encryption without bootstrapping. Cryptology ePrint Archive, Report 2011/277 (2011).
Brakerski, Zvika, and Vinod Vaikuntanathan. "Efficient fully homomorphic encryption from (standard) LWE." SIAM Journal on Computing 43.2 (2014): 831-871.
Brakerski, Zvika, and Vinod Vaikuntanathan. "Fully homomorphic encryption from ring-LWE and security for key dependent messages." Advances in Cryptology—CRYPTO 2011. Springer Berlin Heidelberg, 2011. 505-524.
Brakerski, Zvika, and Vinod Vaikuntanathan. "Lattice-based FHE as secure as PKE." Proceedings of the 5th conference on Innovations in theoretical computer science. ACM, 2014.
Cash, David, et al. "Highly-scalable searchable symmetric encryption with support for boolean queries." Advances in Cryptology—CRYPTO 2013. Springer Berlin Heidelberg, 2013. 353-373.
Coron, Jean-Sebastien, et al. "Fully homomorphic encryption over the integers with shorter public keys." Advances in Cryptology—CRYPTO 2011. Springer Berlin Heidelberg, 2011. 487-504.
Cousins, David Bruce, et al. "An update on SIPHER (Scalable Implementation of Primitives for Homomorphic Encryption)—FPGA implementation using Simulink." High Performance Extreme Computing (HPEC), 2012 IEEE Conference on. IEEE, 2012.
Darpa. "Programming Computation on Encrypted Data (Proceed)", 2010. www.darpa.mil/Our_Work/I2O/Programs/PROgramming_Computation_on_EncryptEd_Data_(PROCEED).aspx. Accessed on Mar. 16, 2014.
Doröz, Yarkin, Berk Sunar, and Ghaith Hammouri. "Bandwidth efficient PIR from NTRU." Financial Cryptography and Data Security. Springer Berlin Heidelberg, 2014. 195-207.
Ducas et al., "FHE Bootstrapping in less than a second" University of California, San Diego {lducas, daniele}@eng.ucsd.edu; 21 pages.
Fotiou, N., et al. "Enhancing information lookup privacy through homomorphic encryption." Security and Communication Networks 7.12 (2014): 2804-2814.
Gentry, C. (2009) Fully homomorphic encryption using ideal lattices. STOC 2009. ACM, New York, pp. 169-178.
Gentry, Craig, Amit Sahai, and Brent Waters. "Homomorphic encryption from learning with errors: Conceptually-simpler, asymptotically-faster, attribute-based." Advances in Cryptology—CRYPTO 2013. Springer Berlin Heidelberg, 2013. 75-92.
Gentry, Craig, Shai Halevi, and Nigel P. Smart. "Homomorphic evaluation of the AES circuit." Advances in Cryptology—CRYPTO 2012. Springer Berlin Heidelberg, 2012. 850-867.
Gentry, Craig. A fully homomorphic encryption scheme. Diss. Stanford University, 2009.
Gordon Cormack and Tom Lynam. SPAM Track Guidelines, 2007. plg.uwaterloo.ca/~gvcormac/spam/.

(56) References Cited

OTHER PUBLICATIONS

Graepel, Thore, Kristin Lauter, and Michael Naehrig. "ML confidential: Machine learning on encrypted data." Information Security and Cryptology—ICISC 2012. Springer Berlin Heidelberg, Jan. 21, 2013.

Halevi, Shai, and Victor Shoup. "Design and Implementation of a Homomorphic—Encryption Library." (2013).

Hayes, Brian. "Alice and Bob in cipherspace." American Scientist 100.5 (2012): 1. 7 pages.

Heckerman, David, Eric Horvitz, Mehran Sahami, and Susan Dumais. "A Bayesian approach to filtering junk e-mail." In Proceeding of AAAI-98 Workshop on Learning for Text Categorization, pp. 55-62. 1998.

Hoffstein, Jeffrey, Jill Pipher, and Joseph H. Silverman. "NTRU: A ring-based public key cryptosystem." Algorithmic number theory. Springer Berlin Heidelberg, 1998. 267-288.

Lindner, Richard, and Chris Peikert. "Better key sizes (and attacks) for LWE-based encryption." Topics in Cryptology—CT-RSA 2011. Springer Berlin Heidelberg, 2011. 319-339.

Lyubashevsky, Vadim, Chris Peikert, and Oded Regev. "On ideal lattices and learning with errors over rings." Journal of the ACM (JACM) 60.6 (2013): 43.

Melchor, Carlos Aguilar. "High-Speed Single-Database PIR Implementation." The 8th Privacy Enhancing Technologies Symposium (PETS 2008). 2008. 10 pages.

Naehrig, Michael, Kristin Lauter, and Vinod Vaikuntanathan. "Can homomorphic encryption be practical?." Proceedings of the 3rd ACM workshop on Cloud computing security workshop. ACM, 2011.

Oppenheim, A.V., Schafer, R.W. Discrete-Time Signal Processing. Pearson Education, 2006.

Paillier, Pascal. "Public-key cryptosystems based on composite degree residuosity classes." Advances in cryptology—EUROCRYPT'99. Springer Berlin Heidelberg, 1999.

Perl, Henning, Michael Brenner, and Matthew Smith. "Poster: an implementation of the fully homomorphic Smart-Vercauteren cryptosystem." Proceedings of the 18th ACM conference on Computer and communications security. ACM, 2011.

Perl, Henning, Michael Brenner, and Matthew Smith. "Scarab library, 2011" Available under the MIT license at https://hcrypt.com/scarab-library/.

Popa, Raluca Ada, et al. "CryptDB: protecting confidentiality with encrypted query processing." Proceedings of the Twenty-Third ACM Symposium on Operating Systems Principles. ACM, 2011. 85-100.

Regev, Oded. "On lattices, learning with errors, random linear codes, and cryptography." Journal of the ACM (JACM) 56.6 (2009): 34.

Rivest, Ronald L., Adi Shamir, and Len Adleman. "A method for obtaining digital signatures and public-key cryptosystems." Communications of the ACM 21.2 (1978): 120-126.

Rusli, E. M. A Darpa Director on Fully Homomorphic Encryption (or One Way the U.S. Could Collect Data), Mar. 9, 2014. http://blogs.wsj.com/digits/2014/03/09/a-darpa-director-on-fully-homomorphic-encryption-or-one-way-the-u-s-could-collect-data/.

Schonhage, Doz Dr A., and Volker Strassen. "Schnelle multiplikation grosser zahlen." Computing 7.3-4 (1971): 281-292.

Solinas, J. A. Generalized Mersenne Numbers. Tech. Rep. CORR 99-39, University of Waterloo, 1999.

Van Dijk, Marten, et al. "Fully homomorphic encryption over the integers." Advances in cryptology—EUROCRYPT 2010. Springer Berlin Heidelberg, 2010. 24-43.

Wang et al. Exploring the Feasibility of Fully Homomorphic Encryption. vol. 99. IEEE Computer Society, Los Alamitos, CA, USA, 2013, pp. 1-10.

Wang, Wei, et al. "Accelerating fully homomorphic encryption on GPUs." Proceedings of the IEEE High Performance Extreme Computing Conference. 2012. 6 pages.

Wang, Wei, et al. "Accelerating fully homomorphic encryption using GPU." High Performance Extreme Computing (HPEC), 2012 IEEE Conference on. IEEE, 2012. 5 pages.

Wikipedia. Naive Bayes spam filtering. https://en.wikipedia.org/wiki/Naive_Bayes_spam_filtering.

Yuqi Wang et al. "Symmetric Ternary Quantum Homomorphic Encryption Schemes Based on the Ternary Quantum One-Time Pad", arxiv.org, Cornell University Library, 201 Olin Library Cornell University Ithaca, NY 14853, May 12, 2015, XP081337576.

Anonymous. "Homomorphic encryption—Wikipedia", Aug. 17, 2015, XP055336752, Retrieved from the Internet: URL: https://en.wikipedia.org/w/index.php?title=Homomorphic_encryption&oldid=676450453.

Yasuda, Masaya, et al. "Packed homomorphic encryption based on ideal lattices and its application to biometrics." Security Engineering and Intelligence Informatics. Springer Berlin Heidelberg, 2013. 55-74.

Yasuda, Masaya, et al. "Secure pattern matching using somewhat homomorphic encryption." Proceedings of the 2013 ACM workshop on Cloud computing security. ACM, 2013. 65-76.

Yi, Xun, et al. "Single-database private information retrieval from fully homomorphic encryption." Knowledge and Data Engineering, IEEE Transactions on 25.5 (2013): 1125-1134.

\* cited by examiner $$a_{g,d,x,g} = \begin{pmatrix} 0 & 0 & \cdots & 0 & 0 & \cdots & 0 & 0 & \cdots & -1 & 2 & \cdots & 2^{t-1} \\ \vdots & \vdots & & \vdots & \vdots & & \vdots & \vdots & & \vdots & \vdots & & \vdots \\ 0 & 0 & \cdots & -1 & 0 & \cdots & 0 & 1 & \cdots & 0 & 0 & \cdots & 0 \\ 0 & 0 & \cdots & 0 & -1 & 2 & \cdots & 2^{t-1} & 0 & 0 & \cdots & 0 & 0 \\ -1 & 2 & \cdots & 2^{t-1} & 0 & 0 & \cdots & 0 & 0 & \cdots & 0 & 0 & \cdots & 0 \end{pmatrix}$$

FIG. 6A

$pk = h_{1 \times 1} = g_{1 \times 1} \cdot f_{1 \times 1}^{-1} \in R_q$    $sk = f_{1 \times 1} \in R_q$

FIG. 6B

$C_{l \times 1} = \mu \cdot \text{BDI}(I_{l \times l}) + S_{l \times 1} \cdot h_{1 \times 1} + E_{l \times 1}$

FIG. 6C

$C_{1 \times 1} \cdot f_{1 \times 1} = (\mu \cdot \text{BDI}(I_{l \times l})$
$\quad + S_{l \times 1} \cdot h_{1 \times 1} + E_{l \times 1}) \cdot f_{1 \times 1}$
$= \mu \cdot \text{BDI}(I_{l \times l}) \cdot f_{1 \times 1}$
$\quad + S_{l \times 1} \cdot h_{1 \times 1} \cdot f_{1 \times 1} + E_{l \times 1} \cdot f_{1 \times 1}$
$= \mu \cdot \text{BDI}(I_{l \times l}) \cdot f_{1 \times 1}$
$\quad + S_{l \times 1} \cdot g_{1 \times 1} + E_{l \times 1} \cdot f_{1 \times 1}$
$= \mu \cdot \text{BDI}(I_{l \times l}) \cdot f_{1 \times 1} + error$

FIG. 6D

$\text{BD}(C) \cdot D \cdot f = \text{BD}(C) \cdot (\mu_2 \cdot \text{BDI}(I) + S_2 \cdot h + E_2) \cdot f$
$= \text{BD}(C) \cdot (\mu_2 \cdot \text{BDI}(I) \cdot f + S_2 \cdot g + E_2 \cdot f)$
$= \mu_2 \cdot C \cdot f + \text{BD}(C) \cdot (S_2 \cdot g + E_2 \cdot f)$
$= \mu_2 \cdot (\mu_1 \cdot \text{BDI}(I) \cdot f + S_1 \cdot g + E_1 \cdot f)$
$\quad + \text{BD}(C) \cdot (S_2 \cdot g + E_2 \cdot f)$
$= \mu_2 \cdot \mu_1 \cdot \text{BDI}(I) \cdot f + \mu_2 \cdot (S_1 \cdot g + E_1 \cdot f)$
$\quad + \text{BD}(C) \cdot (S_2 \cdot g + E_2 \cdot f)$
$= \mu_2 \cdot \mu_1 \cdot \text{BDI}(I) \cdot f + \mu_2 \cdot error_1$
$\quad + \text{BD}(C) \cdot error_2$
$= \mu_2 \cdot \mu_1 \cdot \text{BDI}(I) \cdot f + error$

FIG. 6E

| Parameter | RLWE | Present Invention |
|---|---|---|
| $\lambda$ | | 80 |
| $n$ | | 1024 |
| $\ell$ | | 31 |
| $\sigma_k, \sigma_c$ | | 10 |
| SK size | $n \times \ell = 3.968\ K\ Bytes$ | |
| PK size | $n \times \ell = 3.968\ K\ Bytes$ | |
| Cixt size | $\ell \times n \times \ell = 123.008\ K\ Bytes$ | |

FIG. 7

$$error_f(B, n, q) < q/2$$

FIG. 6F

$$n > \log q(\lambda + 110)/7.2$$

FIG. 6G

$$\mu = \sum_{i=0}^{\ell} \mu_i \cdot 2^i$$

FIG. 6H

$$x_0 = b_0(1 - a_0) \quad y_0 = c_0(1 - b_0) \quad z_0 = 0$$

| Item | Specification |
|---|---|
| CPU | Intel Core-i7 5930K |
| # of CPU Cores | 4 |
| # of Threads | 8 |
| CPU Frequency | 3.5 GHz |
| Cache Size | 15 MB |
| System Memory | 32 GB DDR4 |
| Operating System | Windows 8.1 64-bits |
| Programming IDE | Visual Studio 2012 Ultimate edition |
| GPU | NVIDIA GeForce GTX1080 |
| Maxwell Version | GM204 |
| # of CUDA Cores | 2048 |
| GPU Core Frequency | 1126 MHz |
| GPU Memory | 4 GB |
| GPU L2 Cache | 2 MB |

FIG. 8

| Operation | Present Invention (CPU) (msec) | Present Invention (GPU) (msec) | "Khedr 2014" (GPU) (msec) | GPU Speedup over "Khedr 2014" | "Lbos 2014" (CPU) (Sec) | GPU Speedup over "Lbos 2014" | "Lauter 2014" (CPU) (Sec) | GPU Speedup over "Lauter 2014" |
|---|---|---|---|---|---|---|---|---|
| Encrypt | 23 | 0.16 | 23 | 1.43× | 0.58 | 3625× | 0.78 | 4875× |
| Decrypt | 5 | 1 | 5 | 5× | 0.55 | 550× | 0.74 | 740× |
| Add | 0.25 | 0.07 | 0.2 | 2.85× | 0.001 | 14.29× | 0.003 | 42.86× |
| Multiply | 87.8 | 0.838 | 3.477 | 4.15× | 5.1 | 6085.92× | 0.24 | 286.4× |

FIG. 9

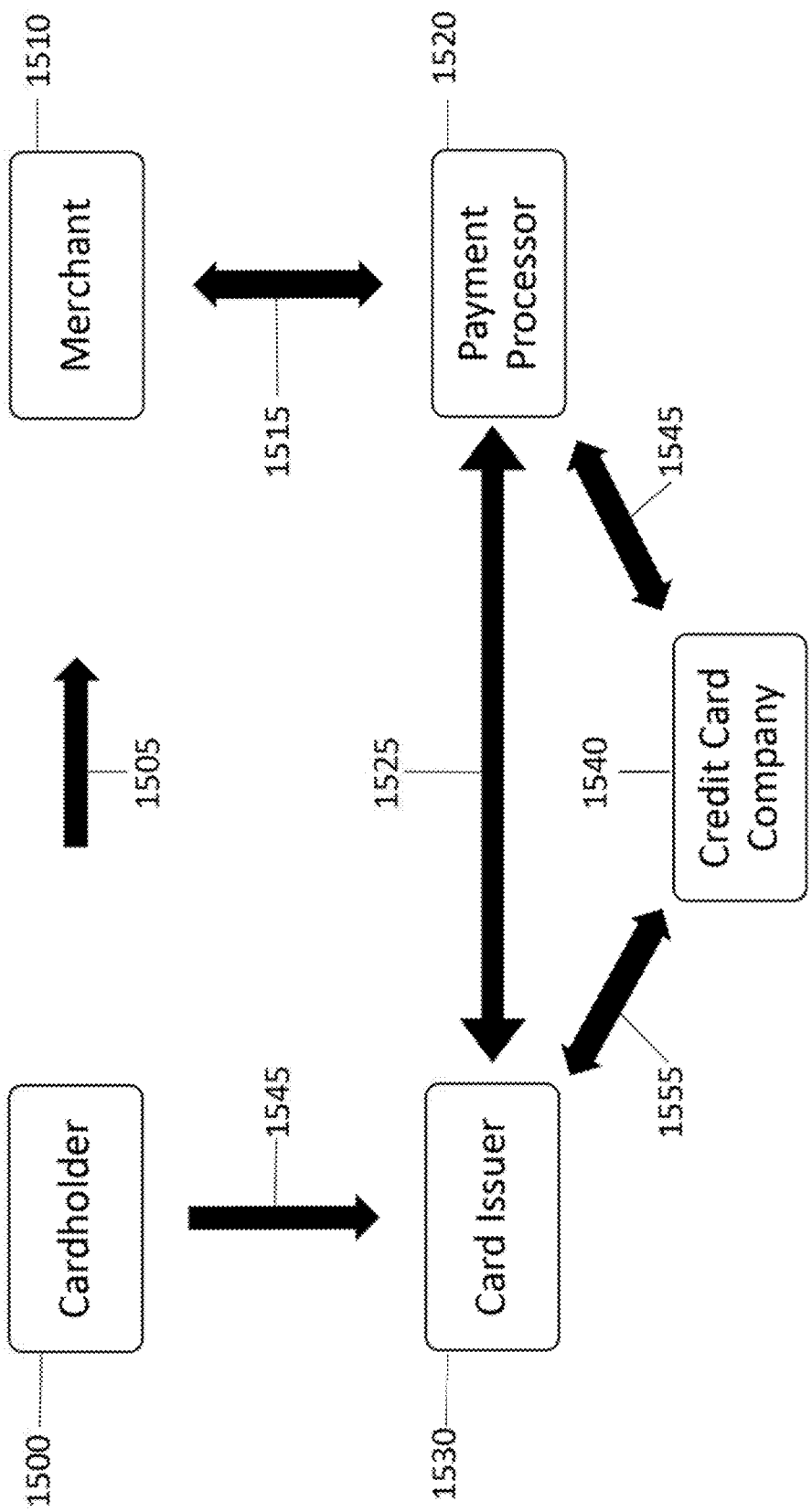

```
Function : Multiply "v" Ciphertexts Function
    Input: "v", Ctxts: C_1, C_2, ..., C_v
    Output: C_return
        The multiplication result of "v" input Ctxts.

C_return = C_1
    For i from 2 to v {
        C_return = C_return × C_i
    }
    Return C_return
```

FIG. 15

Parameter Selection and Keys/Ctxt Sizes.

| Parameter | EXAMPLE SELECTION |
|---|---|
| $\lambda$ | 80 |
| $n$ | 1024 |
| $\ell$ | 31 |
| $N$ | $2 \cdot \ell = 62$ |
| $\sigma_k, \sigma_c$ | 10 |
| SK size | $2 \times n \times \ell = 7.936\ KBytes$ |
| PK size | $2 \times n \times \ell = 7.936\ KBytes$ |
| Ctxt size | $N \times 2 \times n \times \ell = 492.032\ KBytes$ |

FIG. 16

$$A_{1\times 2} \cdot s_{2\times 1} = b - a \cdot t = e$$

FIG. 17A $$C_{N\times 2} = \mu \cdot \text{BDI}(I_{N\times N}) + r_{N\times 1} \cdot A_{1\times 2} + E_{N\times 2}$$

FIG. 17B $$\begin{aligned}
C_{N\times 2} \cdot s_{2\times 1} &= (\mu \cdot \text{BDI}(I_{N\times N}) \\
&\quad + r_{N\times 1} \cdot A_{1\times 2} + E_{N\times 2}) \cdot s_{2\times 1} \\
&= \mu \cdot \text{BDI}(I_{N\times N}) \cdot s_{2\times 1} \\
&\quad + r_{N\times 1} \cdot A_{1\times 2} \cdot s_{2\times 1} + E_{N\times 2} \cdot s_{2\times 1} \\
&= \mu \cdot \text{BDI}(I_{N\times N}) \cdot s_{2\times 1} \\
&\quad + r_{N\times 1} \cdot e + E_{N\times 2} \cdot s_{2\times 1} \\
&= \mu \cdot \text{BDI}(I_{N\times N}) \cdot s_{2\times 1} + \text{error}
\end{aligned}$$

FIG. 17C $$\begin{aligned}
\text{BD}(C) \cdot D \cdot s &= \text{BD}(C) \cdot (\mu_2 \cdot \text{BDI}(I) + r_2 \cdot A + E_2) \cdot s \\
&= \text{BD}(C) \cdot (\mu_2 \cdot \text{BDI}(I) \cdot s + r_2 \cdot e + E_2 \cdot s) \\
&= \mu_2 \cdot C \cdot s + \text{BD}(C) \cdot (r_2 \cdot e + E_2 \cdot s) \\
&= \mu_2 \cdot (\mu_1 \cdot \text{BDI}(I) \cdot s + r_1 \cdot e + E_1 \cdot s) \\
&\quad + \text{BD}(C) \cdot (r_2 \cdot e + E_2 \cdot s) \\
&= \mu_2 \cdot \mu_1 \cdot \text{BDI}(I) \cdot s + \mu_2 \cdot (r_1 \cdot e + E_1 \cdot s) \\
&\quad + \text{BD}(C) \cdot (r_2 \cdot e + E_2 \cdot s) \\
&= \mu_2 \cdot \mu_1 \cdot \text{BDI}(I) \cdot s + \mu_2 \cdot \text{error}_1 \\
&\quad + \text{BD}(C) \cdot \text{error}_2 \\
&= \mu_2 \cdot \mu_1 \cdot \text{BDI}(I) \cdot s + \text{error}
\end{aligned}$$

FIG. 17D $$F(x_1, \ldots, x_p) = \sum_{(y_1, \ldots, y_p) \in S} \left( \prod_{i=1}^{p} \overline{(x_i \oplus y_i)} \right)$$

FIG. 17E $$\mathrm{error}_f(B, n, q) < q/2$$

FIG. 17F $$n > \log q(\lambda + 110)/7.2$$

FIG. 17G

SYSTEM AND METHODS FOR VALIDATING AND PERFORMING OPERATIONS ON HOMOMORPHICALLY ENCRYPTED DATA

FIELD OF THE INVENTION

This disclosure relates to homomorphically encrypted data systems and methods, and more specifically, to validation of, and performing operations on, homomorphically encrypted confidential data without decryption of the confidential data, such as financial data.

BACKGROUND OF THE INVENTION

Privacy of sensitive personal information is an increasingly important topic as more personal data is transmitted and shared, particular via the use of wireless transmissions and cloud data services. Privacy issues arise due to the fear of having a security breach on cloud servers or due to the fear that the service providers themselves misuse this sensitive information. Standard encryption schemes try to address these concerns by devising encryption schemes that are harder to break, yet they do not solve the possible misuse of this sensitive data by the service providers themselves.

While privacy of confidential and personal data, such as financial data, is a paramount concern, access to this data for legitimate purposes, such as to execute a financial transaction, is also needed.

Accordingly, there is a need for improvement in the art.

SUMMARY OF THE INVENTION

According to an embodiment of the invention, there is provided a method of processing a secure financial transaction, comprising: receiving a transaction request to complete a financial transaction, with at least a portion of the request encrypted according to a homomorphic encryption scheme, and the transaction request comprising confidential cardholder data including an account number, non-confidential cardholder data and transaction data; retrieving one or more sets of encrypted comparison cardholder data encrypted according to a homomorphic encryption scheme; comparing the encrypted confidential cardholder data to each set of the encrypted comparison cardholder data using one or more homomorphic operations to determine which set of comparison cardholder data matches the confidential cardholder data and validating the confidential cardholder data; generating an encrypted indicator indicating authorization or rejection of the request to complete the financial transaction based upon at least the validation of the confidential cardholder data; and forwarding the encrypted indicator indicating authorization or rejection of the request to complete the financial transaction to a party seeking authorization to complete the financial transaction, wherein the confidential cardholder data is never decrypted during the method.

According to a further embodiment of the invention, there is provided a non-transient computer-readable medium containing computer-readable instructions which when executed by a computer processor perform the method of: receiving a transaction request to complete a financial transaction, with at least a portion of the request encrypted according to a homomorphic encryption scheme, and the transaction request comprising confidential cardholder data including an account number, non-confidential cardholder data and transaction data; retrieving one or more sets of encrypted comparison cardholder data encrypted according to a homomorphic encryption scheme; comparing the confidential cardholder data to each set of the comparison cardholder data using one or more homomorphic operations to determine which set of comparison cardholder data matches the confidential cardholder data and validating the confidential cardholder data; generating an encrypted indicator indicating authorization or rejection of the request to complete the financial transaction based upon at least the validation of the confidential cardholder data; and forwarding the encrypted indicator indicating authorization or rejection of the request to complete the financial transaction to a party seeking authorization to complete the financial transaction, wherein the confidential cardholder data is never decrypted during the method.

Other aspects and features according to the present application will become apparent to those ordinarily skilled in the art upon review of the following description of embodiments of the invention in conjunction with the accompanying figures.

BRIEF DESCRIPTION OF THE DRAWINGS

The drawings illustrate, by way of example only, embodiments of the present disclosure.

FIGS. 6A-6J show equations for performing computations according to an embodiment of the present invention;

FIG. 7 is a table of data used in an example for an embodiment of the present invention;

FIGS. 8 and 9 show testing parameters and results of tests conducted;

FIG. 10 is a diagram of a four-party credit card transaction system;

FIG. 15 shows pseudocode for a ciphertext multiplication operation;

FIG. 16 is a table of example parameter selection according to an embodiment of the present invention; and FIGS. 17A-17G show expressions/equations according to an embodiment of the present invention.

Like reference numerals indicate like or corresponding elements in the drawings.

DETAILED DESCRIPTION OF THE EMBODIMENTS

Figure 1:
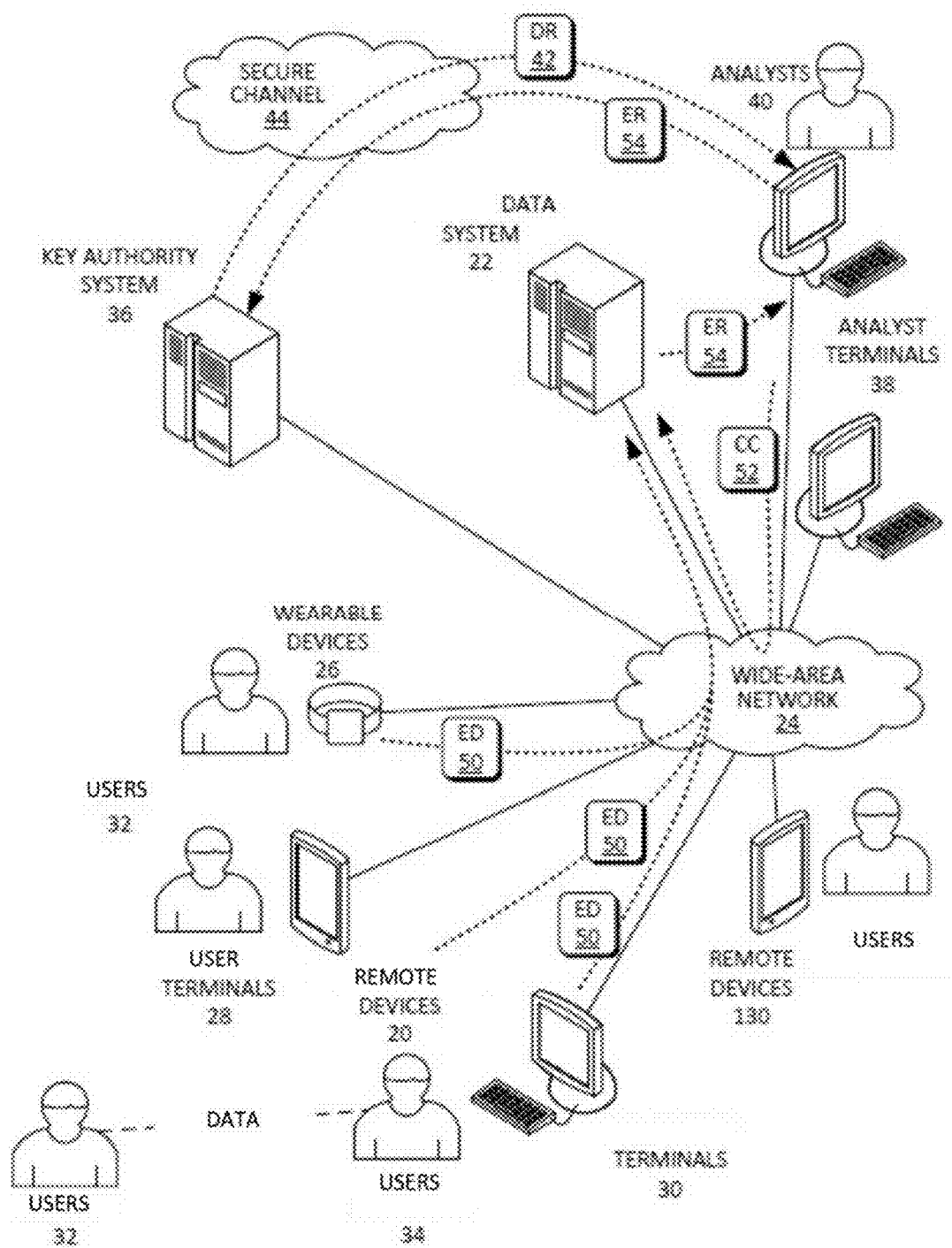
FIG. 1 is a diagram of a secure computing environment according to an embodiment of the present invention.

Although financial applications form the basis of the inventive examples discussed herein, the inventive techniques discussed have application to other forms of confidential data. In this context, the different devices and parties involved in data acquisition, storage, and analysis may be reconsidered as appropriate for the type of confidential data being processed.

Homomorphic Encryption/Decryption

The homomorphic encryption/decryption operations executed on confidential data may be performed as shown in FIGS. 1-5 and FIGS. 6A-6J. Key generation may be performed at a secure system, such as the key authority system 36. Public keys 68 may be pre-loaded onto the remote devices 20 containing the confidential information (such as a credit card, remote sensor, etc.) prior to deployment of remote devices 20. Alternatively, or additionally, public keys 68 may be made available to the remote devices 20 via a network resource (such as a public cloud), which may be configured to require credential verification or authorization (e.g., user name and password) to access public keys 68. The encryption engines 62 on board the remote devices 20, and in the data system 120, may be configured to implement the homomorphic encryption techniques discussed below. The decryption engine 104 at the key authority system 36 may be configured to implement the homomorphic decryption techniques discussed below. The calculation engine 88 at the data systems 22, 120 may be configured to implement the computational techniques discussed below, including the storage and processing of equations, calculation parameters, upper/lower bounds, and intermediate/accumulated results.

Regarding notation for the below discussion, for an odd prime number q, the ring Z/qZ (or $Z_q$) with the interval $(-q/2, q/2) \cap Z$ is identified. The notation $[x]_q$ denotes reducing x modulo q. The examples discussed herein use polynomial rings defined by the quotient polynomials $R=Z[X]/\Phi_m(X)$, where $\Phi_m(X)=x_n+1$ is the irreducible $m^{th}$ cyclotomic polynomial, in which n is a power of 2 and m=2 n. Let $R_q=R/qR$. Any type of multiplication including matrix and polynomial multiplication is denoted herein by the multiplication operator '·'. Rounding up to the nearest integer is denoted by |a|. Matrices of rings are defined as $A_{M \times N}$, where $A_{ij} \in R_q$ and M, N are the matrix dimensions. $I\ell_\times \ell$ represents the identity matrix of rings. Row vectors are represented as [a b], where a and b are the vector elements. Column vectors on the other hand are represented as [a; b].

The parameters of the cryptographic scheme are n, the degree of the number field; q, the modulus; $\sigma_k$ and $\sigma_c$, the standard deviation of the discrete Gaussian error distribution in the keyspace and ciphertext space, respectively; $\ell \triangleq \lceil \log q \rceil$ that governs the number of ring elements in a ciphertext. The setting of these parameters depends on the security level $\lambda$ (e.g., $\lambda=80$ or 128 bits) as well as the complexity of functions contemplated to evaluate on ciphertexts.

A bit decompose function BD(integer) takes an l-bit input integer, then outputs a row vector with size $\ell$ containing the bit decomposition of this integer. (Note that the letter "$\ell$" referred to herein, including the figures, is a lowercase script letter "L".) Similarly, BD(polynomial) takes an input polynomial of size n, where each coefficient is an $\ell$-bit integer, then outputs an $\ell$-sized row vector of polynomials (each of size n) containing the bit decomposition of each coefficient of the input polynomial, yielding a matrix of size $\ell \times n$. Finally, BD(Matrix of polynomials) takes an input matrix of polynomials of size x×y (each polynomial is of size n with integer coefficients), then outputs a matrix of polynomials expanded by a factor $\ell$ in the column dimension, yielding a matrix of size $x \times y\ell$, where each consecutive $\ell$ elements along the row contain the bit representation of each coefficient of each of the input polynomials. For example, the bit decompose of the input polynomial matrix $B_{x \times y \times n}$ is $BD(B_{x \times y \times n}) = \beta_{x \times y \ell \times n}$. It is noted that despite the fact that the polynomial coefficients of matrix $\beta_{x \times y} \ell_{\times n}$ are single bit values, the storage requirement of matrix $\beta$ in CPU or GPU memory is not equal to $x \times y \ell \times n$ bits. This is due to the fact that the smallest addressable unit of memory is a byte (i.e., Byte Addressable). Hence, $\beta$ requires $x \times y \ell \times n$ bytes of storage. This results in the further observation that the storage requirement of $\beta_{x \times y} \ell_{\times n}$ is at least 8 times the storage requirement of $B_{x \times y \times n}$.

A bit decompose Inverse function BDI( ) is the inverse of the bit decompose function BD( ). The BDI( ) function groups consecutive $\ell$ coefficients along a row (the coefficients don't need to be binary), and outputs the integer corresponding to those $\ell$ bits. Mathematically, the BDI( ) function can be defined as multiplying the expanded matrix of polynomials $\beta_{x \times y} \ell$ from the right by the matrix $\alpha_{y\ell \times y}$ defined in the equation of FIG. 6A. (The polynomial dimension n is omitted from this point forward for clarity).

Hence $B_{x \times y} = BDI(\beta_{x \times y \ell}) = \beta_{x \times y \ell} \cdot \alpha_{y \ell \times y}$ Ring Learning With Errors (RLWE) Based Encryption Scheme The method and system may employ a RLWE (Ring Learning With Errors) cryptographic scheme, and the general principles of such scheme will now be described. However, this scheme is not particularly limiting and other suitable polynomial-based fully homomorphic cryptographic schemes may be used. Moreover, any gaps in the below would be well understood by those skilled in cryptography in view of the known art.

The system and method is configured to generate keys, encrypt information, and decrypt information.

The key generator is configured to implement a Keygen ($1^\lambda$) function as follows. A polynomial $t \leftarrow D_{R_q,\sigma_k}$ is chosen. The secret key becomes $sk=s_{2 \times 1} \leftarrow [1; -t] \in R_q^2$. The public key is $pk=A_{1 \times 2}=[b\ a]$, based on a uniform sample $a \leftarrow R_q$, $e \leftarrow D_{R_q,\sigma_k}$, set $b=a \cdot t+e$. It is noted that the expression in FIG. 17A holds.

Figure 13:
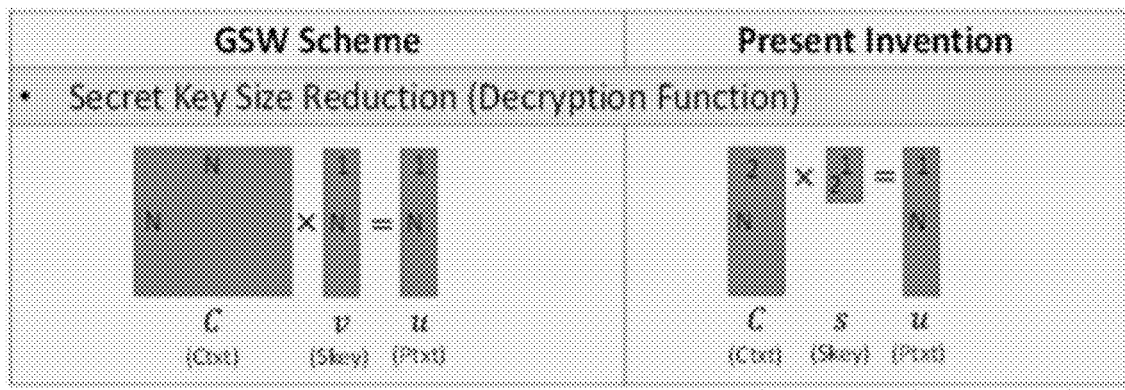
FIG. 13 is a chart showing secret key size reduction according to an embodiment of the present invention.

As shown in FIG. 13, this is advantageous over a known secret key sk=v=PO2 (s) based on a powers-of-two expansion such as PO2 (x) defined as [x, 2x, . . . , $2^{\ell-1}$x]. Hence, the key generator generates smaller secret keys by a theoretical factor of $\ell$ times.

The encryption engine 62 is configured to implement an Enc(pk, μ) function as follows. The message space is $R_q$. A uniform vector $r_{N \times 1}$, is sampled where each coefficient in the polynomials in r sampled from {0,1}, $$E_{N \times 2} \leftarrow D_{R_q,\sigma_c}^{N \times 2}.$$

Figure 14:
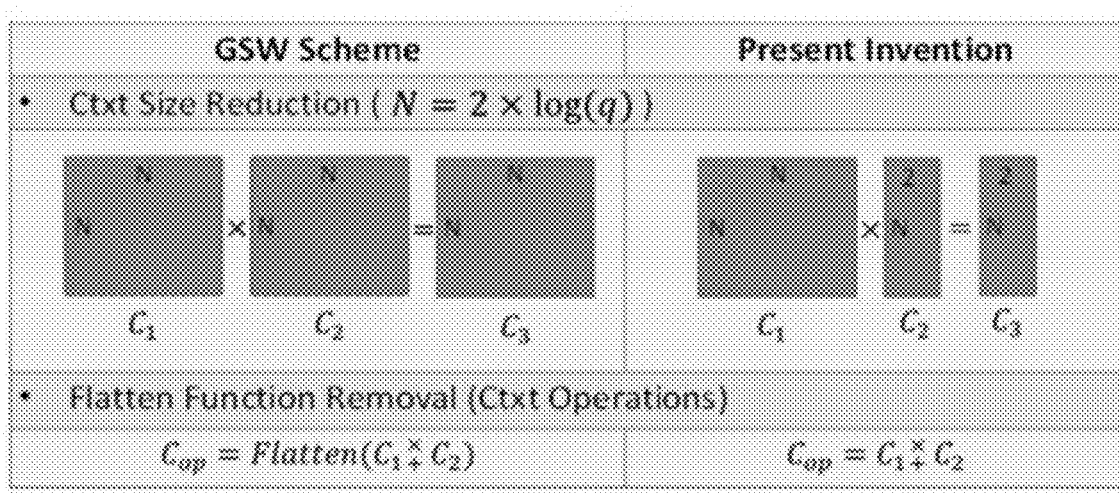
FIG. 14 is a chart showing ciphertext size reduction and obviating a flatten function.

The plaintext polynomial $\mu \in R_q$ is encrypted by calculating the expression in FIG. 17B. As shown in FIG. 14, this is advantageous over prior techniques that use $C_{N \times N}$ as the encryption engine 62 results in smaller ciphertext by a theoretical factor of $\ell$ times.

The decryption engine 104 is configured to implement a Dec(sk, C) function as follows. Given the ciphertext C, the plaintext $\mu \in R_q$ is restored by multiplying C by the secret-key s according to the expression in FIG. 17C.

This is advantageous over prior techniques that implement Dec(sk, C)=$C_{N \times N} \cdot V_{N \times 1}$, as the decryption engine 104 requires the performance of fewer operations a theoretical factor of $\ell$ times.

It is noted that the first $\ell$ coefficients in the first term of the expression in FIG. 17C are in the form $\mu, 2\mu, \ldots, 2^{\ell-1}\mu$. This means that the element at location $i \in [0, \ell-1]$ is in the form $\mu \cdot 2^i$+error. That is, the most significant bit of each entry carries a single bit from the number, $\mu$ assuming that error <q/2 and there is theoretically no wrap-around mod q as may be found in prior techniques.

It is now possible to perform operations on ciphertext without first decrypting the ciphertext. For input ciphertexts $C_{N \times 2}$ and $D_{N \times 2} \in R_q^{N \times 2}$ encrypting $\mu_1$ and $\mu_2$ respectively, homomorphic operations are implemented as follows.

The addition operator implements an ADD(C, D) function to add two ciphertexts $C_{N \times 2}$ and $D_{N \times 2}$ by performing the entry-wise addition $C_{N \times 2} + D_{N \times 2}$.

The multiplication operator and bitwise decomposition function implement a MULT(C, D) function to multiply two ciphertexts $C_{N \times 2}$ and $D_{N \times 2}$ by performing the bitwise decomposition function (or BD) on one ciphertext and then executing the multiplication, as $BD(C_{N \times 2}) \cdot D_{N \times 2}$.

As shown in FIG. 14, this is advantageous over prior techniques that define MULT(C, D)=FLATTEN($C_{N \times N} \cdot D_{N \times N}$), where FLATTEN(A) is defined as BD(BDI(A)). The present technique requires fewer operations by a theoretical factor of at least $\ell$ times.

Correctness of the above homomorphic addition should readily apparent to those skilled in the art. The multiplication is asymmetric in the input ciphertexts C and D. That is, the components of D are treated as a whole, whereas the components of C are broken up into their bit-wise decompositions. The multiplication is correct, as discussed below, and gives a slow noise-growth rate.

The correctness of the multiplication operation should readily apparent to those skilled in the art in view of the expression in FIG. 18D, in which matrix dimensions are removed for clarity. In the last line of the manipulation of expression in FIG. 18D, it is apparent that the encryption of $\mu = \mu_2 \cdot \mu_1$.

Correct decryption depends on the ciphertext noise being bounded. Thus, it is important to understand how homomorphic operations increase ciphertext noise. Taking C as a fresh ciphertext, it is apparent that homomorphic addition of v ciphertexts increases the noise by a factor of v in the worst case. In various contemplated implementations, since the coefficients of the error polynomials are contemplated to follow a Gaussian distribution, the factor is closer to $O(\sqrt{v})$.

It is further apparent that homomorphic multiplication of two ciphertexts $C = Enc(\mu_1)$ and $D = Enc(\mu_2)$ with error magnitudes $B_1$ and $B_2$, respectively, increases the error to $O(B_1 \cdot \|\mu_2\|_1 + B_2 \cdot n \log q)$ in the worst case, and $O(B_1 \cdot \|\mu_2\|_1 + B_2 \cdot \sqrt{n \log(q)})$ in various contemplated implementations. Here, $\|\mu\|_1$ denotes the $\ell$ norm of the message polynomial $\mu$. It is advantageous that error dependence on the two ciphertexts is asymmetric, as evident from the above.

To multiply v ciphertexts the order of multiplication is contemplated to play a role in error. In techniques described herein, input $\mu$ will typically be 0 or 1, meaning that the growth is simply additive with respect to $B_1$. Thus, it is advantageous to multiply v ciphertexts with (the same) error level B through an accumulator-like function as shown in FIG. 15, rather than using a binary tree of multiplications, which tends to grow error at superpolynomial rates. The resulting error growth is $O(B \cdot vn \log(q))$ in the worst case, and $O(B \cdot \sqrt{vn \log(q)})$ in various contemplated implementations. Hence, the control logic may be configured to implement accumulative multiplications, as shown in FIG. 15 and as may be required by various contemplated implementations.

For example, reference is now made to the expression in FIG. 17E, in which $x_1 \ldots, x_v$ are v-tuples of input encrypted bits, $y_1, \ldots, y_v$ are v-tuples of bits in some set S, and operation $\overline{(x| \oplus y|)}$ represents binary XNOR between bits $x_i$ and $y_i$. Since the form of the expression in FIG. 17E stipulates that exactly one of the terms may survive (F=1 when $x_1, \ldots, x_v \in S$, otherwise F=0), the small total error growth can result, even though the component computing based on the expression in FIG. 17E may not be able to determine precisely which term will survive.

It is apparent that noise grows to $O(B \cdot vn \log q \cdot |S|)$ in the worst case, or $O(B \cdot \sqrt{vn \log(q) |S|})$ in various contemplated implementations. This is in contrast to $O(B \cdot \sqrt{(n \log(q))^{\log(v)} |S|})$ when using the known Brakerski-Gentry-Vaikuntanathan encryption scheme, implemented in IBM HElib. Indeed, such expressions, as in the expression in FIG. 17E, are far from atypical, and they occur quite naturally in evaluating decision trees and PIR-like functions as will be discussed further below.

Another source of improvement afforded by the presently disclosed techniques is evident from the error term $B_1 \cdot \|\mu_2\|_1 + B_2 \cdot n \log q$. When multiplication is performed using an accumulator, as shown in FIG. 15, $B_2$ represents the smaller error in the fresh ciphertexts $C_i$, and $B_1$ represents the larger error in the accumulated ciphertext $C_{accum}$. If $C_i$ encrypts $\mu_2 = 0$, then the larger error term $B_1$ disappears from the error expression.

This error reduction is also apparent from the expression in FIG. 17E. When evaluating each of the products in the expression in FIG. 17E, the error can be seen to grow proportional not to v, the total number of multiplications, but rather with k, the longest continuous chain of 1's starting from the end. It is contemplated that this is because the last time a zero is encountered in the multiplication chain, the error is reduced, by the observation above. Assuming that S is an expected set, the expected length of a continuous chain of trailing 1's is $\Sigma_{i=1}^{v} i \cdot 2^i < 2$. In other words, the multiplicative factor of v disappears from the error expression as well, and error growth becomes close to $O(B \cdot \sqrt{n \log(q) |S|})$. This is substantially the same effect as if |S| ciphertexts were added.

Further, when $f$ is taken as a function to be evaluated, for example, the expression in FIG. 17E, the error$_f$(B,n,q) denotes how much the error grows when evaluating the function $f$ on ciphertexts in $R_q$ with an initial error of magnitude B. For correct decryption, it is expected that the expression in FIG. 17F holds. Since errors tend to grow slower using the present techniques, q can be set to be correspondingly smaller to meet a security level equivalent to that of prior techniques. Following the analysis of Lindner and Peikert, for a security level of $\lambda$ bits, it is expected that the following expression holds:

$$n > \log q(\lambda + 110)/7.2 \qquad (7)$$

Because log q in the present techniques is smaller, n can be set to be smaller, for the same security level $\lambda$. In turn, a smaller n can result in a error$_f$(B,n,q) that is smaller, leading to an even smaller q, and so on. Suitable parameters are obtained by solving both the above inequalities in FIGS. 17F and 17G together. FIG. 16 summarizes an example of such a parameter selection.

NTRU Based FHE Scheme

As an alternative to the RLWE-based FHE scheme, in some examples of the invention, an NTRU variant of the encryption scheme is used to reduce computational complexity and to speedup operations, as will be detailed below. The encryption system works as follows.

A key generation function, Keygen($1^\lambda$), requires the choosing of two polynomials $f_{1 \times 1}, g_{(1 \times 1)} \leftarrow D_{R_q, \sigma_k}$ such that (a) f is invertible in the ring $R_q$; and (b) f≡1 (mod 2). This can be done by sampling the polynomial f from the distribution $D_{R_q,\sigma_k}$ until it satisfies conditions (a) and (b).

The public key pk and the private (secret) key sk can be computed from the equation shown in FIG. 6B.

For the encryption function, Enc(pk, m), the message space is $R_q$. A plain text polynomial $\mu \in R_q$ is encrypted by evaluating the equation of FIG. 6C, where $S_{l \times 1}$, $E_{l \times 1} \leftarrow D_{R_q,\sigma}^{l \times 1}$, are sampled from a discrete Gaussian distribution with standard deviation $\sigma_c$. This encryption function can be implemented at the encryption engine 62.

Concerning the decryption function, Dec(sk, C), for a given the ciphertext C, the plaintext $\mu \in R_q$ is restored by multiplying C by the secret-key $f$ using the equation of FIG. 6D. This decryption function can be implemented at the decryption engine 104.

With reference to FIG. 6D, the $\ell$ polynomials in the first term of the last line are in the form $\mu f$, $2 \mu f$, ..., $2^{\ell-1} \mu f$. This means that the element at location $i \in [0, \ell-1]$ is in the form $\mu f \cdot 2^i + \text{error}$. That is, the most significant bit of each entry carries a single bit from each coefficient in $\mu f$ assuming that error $< q/2$ and there is no wrap-around mod q as is found in the prior art. As such, "$\mu f$" can be fully recovered from C which can then be multiplied by $f^{-1}$ to recover $\mu$.

In addition to the ability to recover the message polynomial $\mu$, the l ring elements in the ciphertext facilitate and manage noise growth in homomorphic operations (in particular, homomorphic multiplication) as described below.

Regarding homomorphic operations, for input ciphertexts $C_{\ell \times 1}$ and $D_{\ell \times 1} \in R_q^{\ell \times 1}$ encrypting $\mu_1$ and $\mu_2$ respectively, homomorphic operations are defined as follows. For an addition operation, ADD(C, D), to add two ciphertexts $C_{\ell \times 1}$ and $D_{\ell \times 1}$, the output is $C_{\ell \times 1} + D_{\ell \times 1}$, which is an entry-wise addition. For a multiplication operation, MULT (C, D), to multiply two ciphertexts $C_{\ell \times 1}$ and $C_{\ell \times 1}$, output is $BD(D_{\ell \times 1}) \cdot D_{\ell \times 1}$. The addition and multiplication operations can be implemented at the calculation engine 88.

The correctness of the above homomorphic addition and homomorphic multiplication should be apparent to those skilled in the art in view of this disclosure. It is clear that the multiplication operation is asymmetric in the input ciphertexts C and D. That is, the components of D are treated as a whole, whereas the components of C are broken up into their "bit-wise decompositions". It is shown below that this multiplication method is correct and gives a slow noise-growth rate.

The correctness of the multiplication operation is evident from the decryption operation shown in FIG. 6E, in which matrix dimensions are removed for clarity. Note that the last line shown in FIG. 6E is the encryption of $\mu = \mu_2 \cdot \mu_1 \cdot f$. Note also that BD $(C_{\ell \times 1})$. $BDI(I_{\ell \times \ell}) = I_{\ell \times \ell} \cdot C_{\ell \times 1} = C_{\ell \times 1}$.

Concerning noise analysis, taking C as a fresh ciphertext, the following observations can be made in view of the operation shown in FIG. 6E. Homomorphic addition of v ciphertexts increases the noise by a factor of v, in the worst case. In some implementations, since the coefficients of the error polynomials follow a Gaussian distribution, the factor is closer to $O(\sqrt{v})$. In addition, homomorphic multiplication of two ciphertexts C=Enc($\mu_1$) and D=Enc($\mu_2$) with error magnitudes B1 and B2, respectively, increases the error to $O(B_1 \cdot \|\mu_2\|_1 + B_2 n \log(q))$ in the worst case, and $O(B_1 \cdot \|\mu_2\|_1 + B_2 \sqrt{n \log(q)})$ in various contemplated applications. Here, $\|\mu_2\|_1$ denotes the $l_1$ norm of the message polynomial $\mu$. As can be seen, error dependence on the two ciphertexts is asymmetric.

Regarding the setting of parameters, taking f to be a function that is being evaluated and that computes the multiplication of v ciphertexts, error$_f$(B, n, q) denotes how much the error grows when evaluating a function f on ciphertexts in Rq with an initial error of magnitude B. For correct decryption, the equation of FIG. 6F should be satisfied.

Since error in accordance with the present invention may grow slower than in some known schemes and since there may be no need for a chain of moduli to control the noise growth, q can be set to be correspondingly smaller for the same security level afforded by such known schemes. For a security level of $\lambda$ bits, the equation of FIG. 6G should be satisfied.

Figures 6F, 6G, 6H, 6I, 6J, 7:
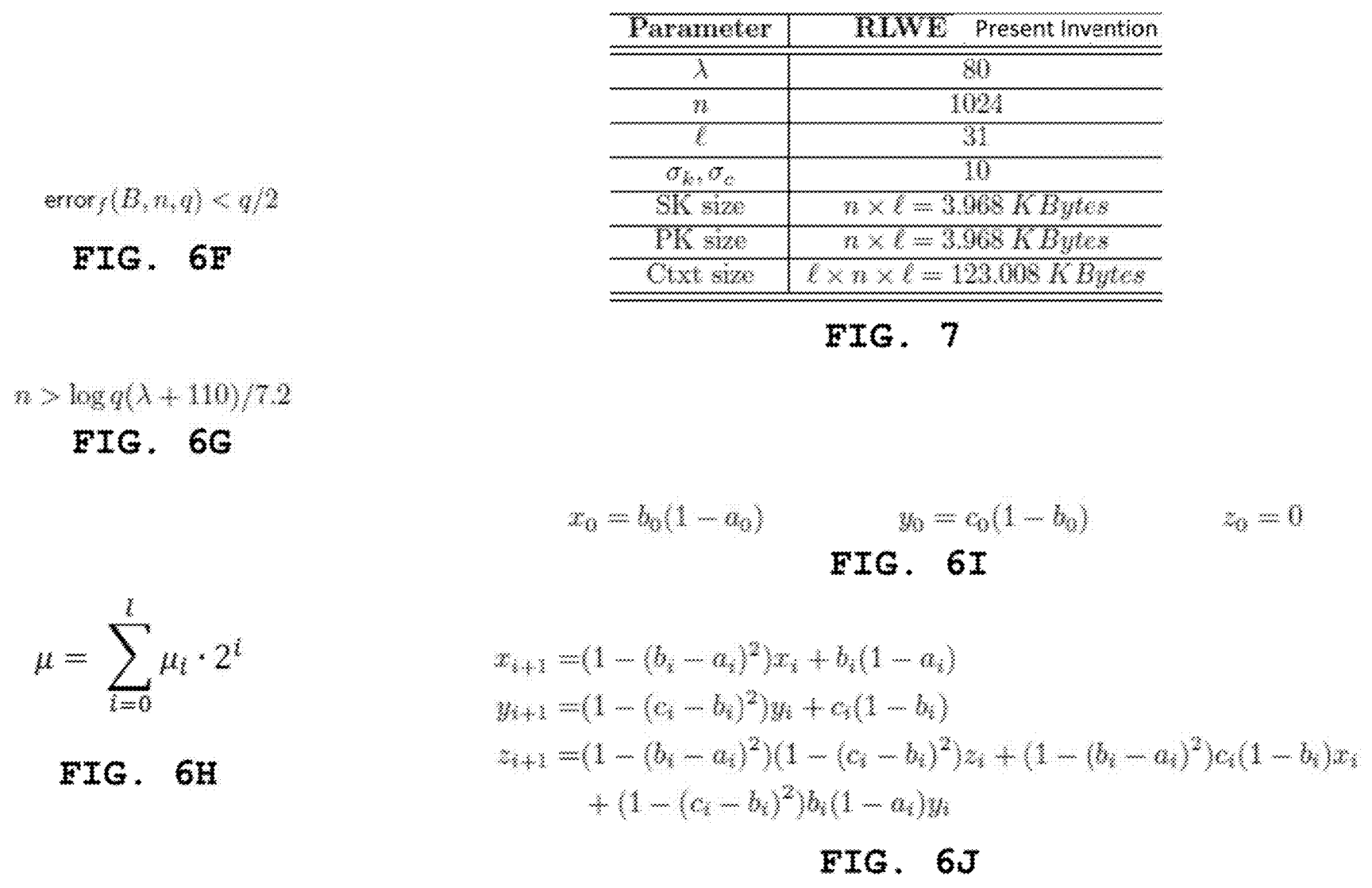

Because log q according to the present invention may be smaller relative to known schemes, n may be set smaller for the same security level $\lambda$. In turn, with a smaller n, the new error$_f$(B, n, q) is smaller, leading to an even smaller q, and so on. Optimal parameters can be obtained by solving the above inequalities of FIGS. 6F and 6G together. The table of FIG. 7 summarizes an example parameter selection.

In addition, the encryption scheme according to the present embodiments does not use the flatten operation introduced by the GSW scheme. A flattened ciphertext (Ctxt) takes up a large memory space. It also needs considerable computation time to combine entries and decompose them back into bits (or even decompose them into groups of "m" bits for a higher radix Bit Decompose operator). Further, since the encryption scheme according to the present invention does not use a flatten operation, it does not have single bits representing ciphertexts. Rather, ciphertexts are represented as packed numbers mod q. To multiply ciphertexts, it is advantageous to use the fast NTT algorithm to speed up the ciphertext multiplication operation, as opposed to using regular polynomial circular convolution. The encryption scheme according to the present embodiment decrypts the most significant bit from all 1 polynomials in the ciphertext, as opposed to decrypting only a single bit from a single polynomial in the ciphertext. In this way 1 bits, one from each polynomial, can be decrypted. These bits are combined back into the encrypted polynomial using the formula shown in FIG. 6H.

Types of encrypted confidential data that can be collected and homomorphic calculations that can be performed thereon are now discussed. Specific data/calculations discussed below include analysis of financial transaction data, particularly credit card data, and evaluation of relational operations. Although some of the examples discussed pertain to specific data, it is noted that some computations can be used for other types of data (e.g., relational operations). Further, it is noted that the examples discussed below are not limiting and other examples within the scope of the present invention are contemplated.

Financial Transactions

One area of application for an embodiment of the homomorphic encryption system is financial transactions, particularly credit card transactions. Attacks on credit card information have escalated tremendously in recent years, with major breaches resulting in millions of client record being exposed. Once exposed, the client information may be resold (e.g. on the dark web), used for fraudulent transactions, particularly card not present (CNP) transactions, or used for direct attacks on Point-of-Sale (POS) systems.

These attacks happen because credit card information, either in the databases or for the client, are present in a plain text format at some point in the credit card authorization process. According to an embodiment of the present invention, the system may encrypt the credit card information from the point at which it is acquired and never decrypt the ciphertext even at the authentication step.

Payment Processing

Major credit card companies, such as VISA™ and MasterCard™, structure bank card transactions in what is called the four-party model. The parties in this model are the cardholder 1500, the merchant 1510 (the service provider), the payment processor 1520 (the acquirer), and the card issuer 1540. In addition, there is potentially a fifth party which is the credit card company (payment brand) 1530 all as shown in FIG. 10.

The transaction starts when the cardholder 1500, who wishes to purchase something, uses his credit card information on an online merchant or presents his credit card 1505 to the merchant 1510 at the store. The merchant 1510, online or using the point of sale system, acquires and encrypts the credit card information and sends it 1515 to the payment processor 1520 over the network. The encryption at the merchant may be done at the POS terminal or may be done using an application installed on the merchant's systems using the public encryption key. The payment processor 1520 then decrypts the credit card information and forwards it 1525 to the card issuer 1530 for authorization. The merchant 1510 charges the credit card and provides the service or product to the cardholder 1500 once the credit card authorization is received. The payment processor 1520 reimburses the merchant for the service, after that, the card issuer 1530 pays back the payment processor 1520 within 24 or 48 hours. A tokenized system may be utilized between the payment processor and the merchant to eliminate the need for the merchant to store the cardholder information. The merchant stores only a token corresponding to either the cardholder account or to the individual transactions.

Information, such as cardholder and transaction data, as well as internal fees, such as network and interchange fees, may be passed 1545 between the payment processor 1520 and credit card company 1540, or between 1555 the card issuer 1530 and credit card company 1540, or both, either as required during the transaction, or after the transaction.

There are multiple points of vulnerability in this credit card system that may allow attackers to steal credit card information.

Point of Sale System (POS): When the cardholder presents his card at the merchant store, his/her card is swiped in a credit card machine or a card reader that transfers this information to a computer. There may be some points in the system where this card information is not encrypted for some time before sending it to the payment processor. At this point, malware installed in the system can gather this information and send it back to the attacker. To address this vulnerability, credit card information must be encrypted the moment it is read using the card reader. This way, malware will not be able to gather card information using this method. Currently, point to point encryption (P2 PE) is used to securely transmit credit card information from the POS system to the payment processor, which then decrypts it to send to the card issuer for verification. P2 PE uses 3 DES or AES for encryption which may be considered safe for the time being but may not be secure against quantum computers in the future.

Payment Processor: When the payment processor receives the encrypted credit card information from the merchant, it decrypts it and sends it in plaintext to the card issuer for authentication. This is a clear point of weakness. Any malware installed in the payment processor system, or any attacker who broke the secure channel between the payment processor and the card issuer, can gather the credit card information while being in plaintext form. To address this vulnerability, credit card information should never be decrypted at any point. Additionally, in the case of a tokenized system, the presence of the secure vault which translates the transaction into a token and vice versa. This vault stores all the cardholder information and their corresponding tokens. If this vault is hacked, valuable information will be at risk.

The card issuer has two points of vulnerability: 1) it receives the client credit card information in plaintext. This exposes it to the possibility of attack; and 2) the card issuer database of credit card information for all its clients sits in a secure server in plaintext to compare it to the incoming card information. This is the largest security threat on credit card information. This is because an attack on this secure database will result in the loss of all credit card information.

These vulnerabilities may be solved if all the credit card information in the database and also the incoming card information in plaintext were encrypted and were compared while in ciphertext.

Figure 11:
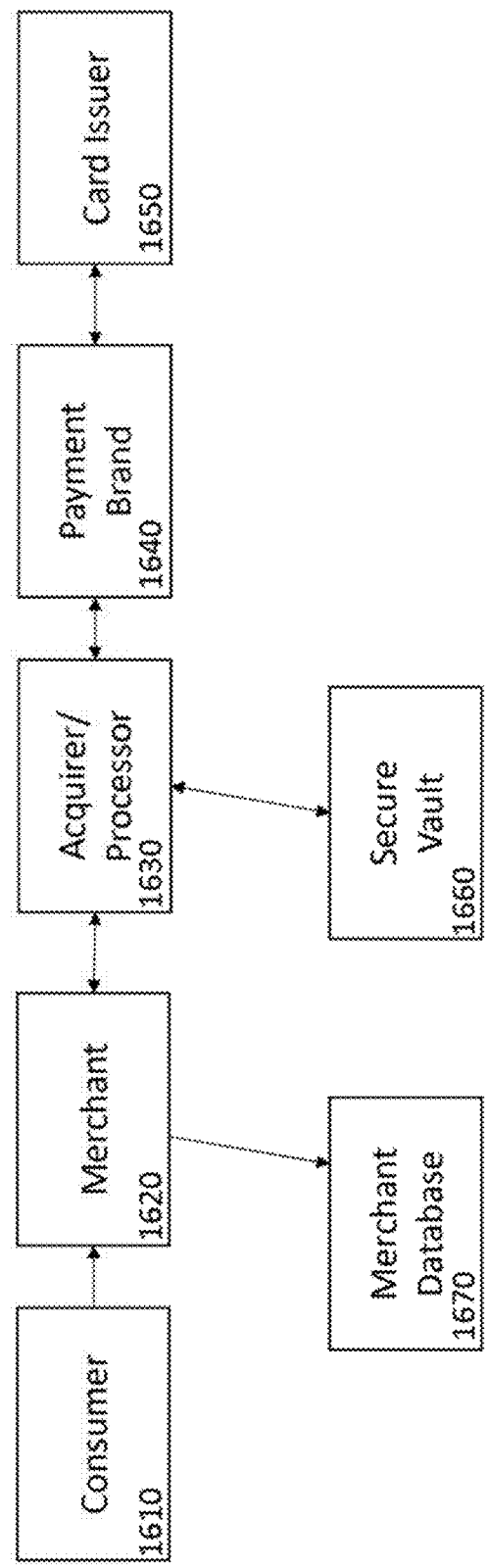
FIG. 11 is a diagram of a payment processing chain according to an embodiment of the present invention.

According to an embodiment as shown in FIG. 11, there is presented an embodiment of the present invention which is a change in the credit card authorization system that may provide a much higher level of security than current systems. The embodied system may be based on encrypting the credit card information at the POS system using quantum secure Fully Homomorphic Encryption (FHE) which is based on lattice based cryptography. The need for FHE is based on the need for both homomorphic addition and multiplication operations on encrypted data. If only one type of operation is required, somewhat homomorphic encryption may be used. Once the card information is encrypted at the online website or at the POS, there may not be a need to decrypt at any point afterwards. The encrypted credit card information may be compared against credit card database data (e.g. sets of cardholder data for various cardholders held in a database) at the card issuer which may also be encrypted using the same FHE encryption.

Thus, the system may eliminate any possible attacks on credit card information, either in the network, or in the database servers because they may all be encrypted using a quantum secure FHE encryption scheme.

The cardholder data from the consumer 1610 (the primary account number (PAN)) is captured by the online transaction data entry (or at the POS), the data is encrypted using a public-key Fully Homomorphic Encryption (FHE) scheme. The credit card number (except for the first digit and the last 4 digits), month, year, and CVV numbers may be encrypted using the FHE public encryption key published by the credit card company. The name of the cardholder and the first digit and the last 4 digits of the credit card number may be encrypted using the regular encryption schemes. The merchant 1620 then sends the encrypted PAN to the acquirer/payment processor 1630.

The payment processor 1630 forwards the encrypted PAN to the appropriate payment brand 1640 using the credit card first digit (e.g., Visa™, MasterCard™, American Express™, etc.). The payment brand 1640 then forwards the encrypted PAN to the card issuer 1650 (issuing bank) using the next five digits (BIN: Bank Identification Number).

The card issuer 1650 may use the cardholder name and last 4 credit card digits to narrow down the credit card entries in the database that match this information. Each entry in the narrowed down list may be enumerated, compared against the encrypted PAN using FHE algorithms, and the encrypted matching indicator will be multiplied by the number corresponding to each entry in the list. The encrypted result from each entry may all be added together to get a final result. The final result may encrypt the number of the matching account, the numbers corresponding to all other accounts will be multiplied by '0' (due to mismatch), which will nullify the result. The encrypted result is sent back to the payment brand 1640, which decrypts it and sends the final result, which is a single digit corresponding to the matching account, back to the card issuer 1650 to verify that the card is not reported lost or stolen, and that the account has the appropriate amount of credit/funds available to pay for the transaction. The card entries may be ordered by most frequently used and the rest of the entries may be ignored once a hit is found to reduce the verification time.

If approved, the issuer 1650 generates an authorization number and routes this number back along with a card-specific FHE encrypted PAN to the payment brand 1640. The payment brand 1640 the forwards the authorization code and the encrypted PAN back to the acquirer/processor 1630.

The acquirer/processor 1630 accesses a secure vault 1660 to retrieve/generate a token corresponding to the encrypted PAN. Note that the secure vault 1660 may also be FHE encrypted except for the tokens.

The acquirer/processor 1630 returns the token back to the merchant 1620. The merchant may retain the token long term in a merchant database 1670 for the processing of returns, retrieval requests or chargebacks, as well as for business intelligence reasons such as analysis of consumer buying behavior and creation of marketing programs.

This embodiment is an example of a centralized system where only one entity, the credit card company 1640, owns the secret decryption key and distributes public encryption keys. Another embodiment is a decentralized system where each card issuer 1650 holds its own secret decryption key and that the POS systems recognize which card issuer the credit card belongs to and encrypts the card's information using the appropriate public encryption key corresponding to this card issuer. This decentralized system may need another entity which is solely responsible for decrypting the encrypted comparison result. This may be required to decouple the card issuer servers holding the encrypted credit card information from the servers which hold the valuable secret decryption key.

Another embodiment is the use of FHE multiparty computation. Different secret keys will be generated for each user and the public key will be stored in the credit card itself. The cardholder data will be encrypted by the user's public key and may be sent to the system for matching against other accounts. Multiple secret decryption keys will be required to decrypt the final result. Additionally, with multiple keys, each party may be limited to decryption only of the information associated with their key, and not be capable of decrypting any other information, improving overall security of the data.

The system may be applied on multiple different levels: the first version is a full system where information is encrypted from the origin and never decrypted at any point in the system.

The second version is a partial system where, in order to accommodate the current payment systems, and to reduce the risk of data attacks, at the payment processor, after card information decryption, card information can be re-encrypted using FHE before sending to the card issuer. This may reduce the possibility of attacks but there is a brief moment in time where data is in the clear between information decryption and re-encryption where data can reside in the device memory vulnerable to attacks. However, the credit card database at the card issuer may always remain encrypted using FHE.

The system also supports online transactions using online payment systems using credit cards or PayPal or other online transaction services where payment information may be encrypted on the client PC prior sending over the Internet.

According to an embodiment, credit cards consist of the following key information: Bank name (Front); Credit card number of 13-19 digits (Front); Credit card expiry date (Front); Cardholder name (Front); and Card Verification Value (CVV) (Back). The credit card number consists of a leading 6-digit Bank Identifier Number (BIN), also known as an Issuer Identifier Number (T N), and a 6- to 12-digit account number, and a single digit checksum number. The terminating 3 digits of the account number and the checksum number are encrypted with the same FHE scheme but using a different key which may be given to specific parties for decryption. Other cards based on a BIN or IIN, such as debit cards, reward cards, and merchant-specific cards may also be used and have an equivalent numbering system.

In an embodiment, the following fields may be encrypted using quantum secure lattice-based Fully Homomorphic Encryption (FHE): the middle 3-9 digits of the credit card number (e.g. the secure portion of the account number), the expiry date and the CVV number. These fields may never be decrypted at any point in the verification process. They may always be in the ciphertext (Ctxt) form.

The remaining items in the credit card may be encrypted using the same encryption scheme but with one or more different public/secret key pairs. A proper key management system is crucial for the overall security of the system. The other keys may be used by intermediate parties to decrypt the needed fields. Though the remaining fields may be encrypted using an FHE scheme, no homomorphic operations may be applied to them. Every character of the remaining fields may be encoded in adjacent coefficients in the same polynomial. The remaining fields are: bank name, cardholder name, and the first 6 digits (BIN number) and last 4 digits of the credit card number.

These remaining fields may be in plaintext (Ptxt) form at some points in the verification process. They help identify the credit card company (first digit) and well as narrow down the credit card entries in the card issuer credit card database (last four digits+Cardholder name). This choice narrows down the probable matching cards to just a few. Additionally, by partitioning the fields, the system may accommodate future changes to the credit card number system, such as the 8-digit and alphanumerical BIN proposals developed by the International Organization for Standardization (ISO).

Additionally, further fields may be included in the transaction request and handled without disruption as, since the data is not decrypted, the actual source and content of the data is not significant, only the ability to validate and authenticate it. Thus, developments such as biometric (e.g. fingerprint) identification, rotating or variable CVV numbers, and one-time card numbers may all be validated and authentication via the present method and system, and, in some cases, without any substantive changes.

As mentioned earlier, some fields in the credit card information may never be decrypted at any time in the verification process. Performing the credit card authentication using these encrypted items uses the properties of the FHE encryption scheme.

Fully homomorphic encryption permits addition and multiplication operations on encrypted data to generate an encrypted result, which, when decrypted, gives the correct result if the same set of operations were applied on unencrypted data.

To perform blind matching between two single bits x and y, it is possible to apply the XNOR binary operation on these two bits $z=\overline{x \oplus y}$. To implement the XNOR operator homomorphically, it needs to be broken down into addition and multiplication operations, specifically, $z=\overline{x|y}=xy+\overline{xy}$.

To match multiple-bit inputs, $x=x_1 x_2 \ldots x_n$ and $y=y_1 y_2 \ldots y_n$, this can simply be done by matching the corresponding, same-order, individual bits, and multiplying the result of the individual bit matching together $z=z_1 \times z_2 \times \ldots \times z_n$. Where the final result z is a single bit indicating if x is equal to y or not.

Implementing the XNOR operation using $\overline{x \oplus y}=xy+\overline{xy}$ is used for other homomorphic encryption schemes which support multiplying multiple accumulator Ctxts (Ctxts that encrypts the result of previous Ctxt multiplications). This multiple accumulator multiplication is not suitable for the embodied encryption scheme since the parameter values are set to be as small as possible, while keeping the security level constant, that it supports multiplying an accumulator only with either fresh Ctxts, or Ctxts that are results from Ctxt addition/subtraction operations. This may reduce the memory and network usage of the Ctxts, and may also speedup Ctxt operations.

To address this, the XNOR operation can be re-written to make it suitable for the embodied encryption scheme. The XNOR is reformulated to be $z=\overline{x \oplus y}=(1-x-y)(1-x-y)$ and applying this formula on x and y will result in $z=1$ only when $x=y$. This addresses the system requirements, since for multi-bit inputs x and y, the matching bit z equals $z=(1-x_1-y_1)(1-x_1-y_1)(1-x_2-y_2)(1-x_2-y_2) \ldots (1-x_n-y_n)(1-x_n-y_n)$. Now each individual bracket consists only of Ctxt addition/subtraction operation which is implementable using the embodied encryption scheme.

Secure relational operation where $z=1$ if $x>y$, and $z=0$ otherwise is also possible using the FHE encryption scheme using the secure relational operations as discussed above in FIGS. 6I and 6J. This can be very useful to also be able to check if the amount needed for the credit card transaction "y" is exceeds the credit limit for this account "x" (or exceeds the account limit in case of a debit card).

According to an embodiment, in performing the secure credit card authentication, the middle digits (for this example, 6 digits for a 16-digit card number are assumed) of the credit card number are first converted into bits where each bit is then encrypted using FHE encryption. The same process is performed for the expiry date and the CVV number. These encrypted bits are then sent on the network along with the cardholder name, bank name, BIN number, and last 4 digits of the credit card to the payment processor which then forwards them to the appropriate card issuer. The card issuer will then receive this information, and using the cardholder name and last 4 digits of the card number, it will narrow down the search to just a few possible matching accounts (due to the match in the name and the last 4 digits) and the corresponding encrypted information will be fetched. Secure authentication is then applied between the incoming encrypted information and the possible matching accounts. The authentication operation done on the non-matching accounts will result in an encrypted indicator which is $z=0$. The matching account, if all the bits of the credit card number, expiry date, and CVV numbers match (and possibly BIN number if used), and if the requested transaction amount is less than the account balance or limit, an encrypted indicator of $z=1$ will be generated. The encrypted indicator, either '0' or '1' can then be multiplied by a number corresponding to the order of this entry against the reduced list. To decrypt this final result and to get a confirmation for this transaction, this encrypted indicator, which encrypts the order of the matching account in the reduced list, needs to be decrypted using the secret decryption key available at the credit card company (or on a separate secure server owned by the card issuer in the case of decentralized scheme). After decryption, only a single digit is returned which corresponds to the order of the matching account in the reduced list.

In another embodiment, the sensitive bits for the input card and for each of the matching accounts are partitioned into "k" parts, where "k" corresponds to the number of processors (e.g. GPUs) available in each machine and each part is sent to a different GPU. Each GPU may be enumerated by a number ranging from 0 to k−1. The result from each GPU may be rotated by a number of polynomial slots corresponding to its GPU number by multiplying by a polynomial with a 1 shifted to the corresponding location. When the results are available from each GPU, all the results are added. This will produce a result where k slots of the encrypted polynomial each has a bit corresponding to a match or non-match for the corresponding bits. After decryption, if all the bits are non-zero, this means that this account is a match. When a matching account is found, it may be put at the top of the list in the database to make matching time faster in the next times, also the remaining accounts may be ignored.

The quantum-secure, lattice-based FHE scheme used for this system may be computationally intensive. To speed up the homomorphic operations, graphical processing units (GPUs) are used alongside the CPUs in the system. Each GPU is capable of supporting a number of transactions per second. To achieve high transactions per second required by large transaction companies like VISA™ and MasterCard™ (each may require up to 4000 transactions per second), many GPU cards are required. To realize such a performance throughput, a multi-server environment may be implemented that can be scaled to serve any level of demand.

Furthermore, while the above embodiment presents a simple matching of the credit card in the transaction request against a list of account names and numbers to determine the presence of a valid account, other lists and types of validation may also take place. For example, there may be a separate list of stolen/lost cards and cardholder data against which the transaction request may be compared as well. In that case, the card number may be valid, but the authentication denied, if the card also appears on the stolen/lost list. A similar process may also be used for other validation and authentication lists, such as blacklisted countries for transaction, while remaining compliant with laws regarding disclosure of such information.

This may also be directed to the benefit of the user and/or merchant as well, such as by matching data in the request to a merchant rewards program, either by extracting the data from the request, or by matching it in a list. This reduces the need for multiple transactions and separate processing, potentially leading to greater transaction efficiency. Further extensions and variations may only be limited by data bandwidth and processing time requirements.

Effectively, any encrypted data may be validated and authenticated against any set of encrypted data without the need for decryption. Changes in the data formats, data structure, or even the data itself may be more easily accommodated, since decryption information need not be shared.

Homomorphic encryption does not natively provide data integrity. Hackers may be able tamper with the encrypted data by apply their mathematical operations on the data while at rest or in motion. This may affect the result of the manipulated data and may change the result to something that may aid the hacker in an attack. For example, applying a homomorphic OR operation on the final encrypted flag with an encrypted "1" which will make the result always a "1" or "Transaction Granted". The protection of data integrity from the modification of unauthorized parties may be provided by applying extra mathematical machinery to provide a tamper resistant credit card authentication system. As an example, without limitation, a Hash-based Message Authentication Code (HMAC) can be appended to the encrypted message to provide the required authentication of the message integrity.

In addition, as an extra security protection layer to the credit card transaction, the system may support encrypting a credit card CVV number that is periodically changing over time. The system may homomorphically encrypt the CVV number generator key and store it in the bank database. When a new customer credit card is to be verified and purchase authorized, mathematical operations are applied homomorphically on the CVV generator key to generate the new valid CVV number to be matched against the customer credit card to be verified.

For example, other forms of static or quasi-static private identification data which required both confidential/encrypted treatment and validation and authentication for a request, may be used within this system and method. Not only bank debit cards (similar data structure to credit cards), but other private identification which is typically found in a card or similar format may be used. As with credit cards, the data deemed confidential and the data which may be shared as cleartext depends on the decisions of the governing body responsible for the identification data, e.g. the government in the case of a passport.

Figure 12:
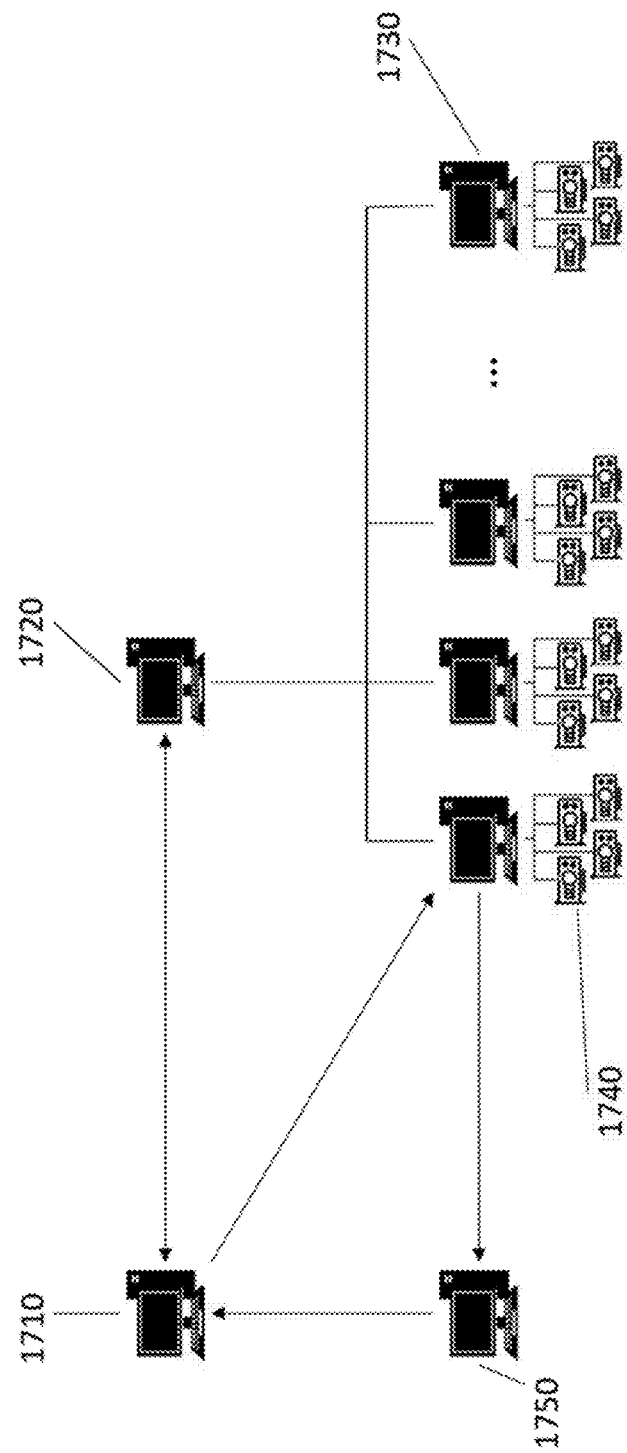
FIG. 12 is a diagram of a secure payment processing system according to an embodiment of the present invention.

The full system according to an embodiment is shown in FIG. 12. The authentication process may take place when the payment processor 1710 sends the credit card information to the card issuer. The card issuer may have a front-end server 1720 that accepts incoming requests. This front-end server 1720 may be connected to a network of GPU machine farms 1730 that send frequent updates to the front-end server 1720 about its occupancy (if it is free or not). When the front-end server 1720 receives a request, it may check its server table for a free machine 1740, and fetch its corresponding IP address. This IP address is then sent back to the payment processor 1710. The payment processor 1710 then connects to this free computing node 1740 and sends the cardholder card information to it. When the computing node 1740 gets that information, it may fetch from the database the data of the credit cards which match the cardholder name and the last four digits. The authentication process may then take place on that GPU on this specific machine 1740. The result of the authentication operation may then be sent to the credit card company 1750 for decryption. The decrypted authentication digit may then be sent back to the card issuer 1710 to indicate the final result. This system may be implemented to ease the network connection requirements for the front-end server 1720 and to distribute it on all the computing nodes 1730.

According to a more general embodiment, FIG. 1 shows a networked computer system embodying various aspects of the present invention for use with confidential data. A plurality of remote devices 20 are connected to a data system 22 via a wide-area network 24. The remote devices 20 may include devices such as wearable devices 26, terminals 28, terminals 30, and the like. Wearable devices 26 may include devices such as special-purpose devices, smart-watches, wearable computers, smart clothing, and similar. Wearable devices 26 may include, but are not limited to, sensors such as global positioning system (GPS) receivers, and similar. Terminals 28 and terminals 30 may include devices such as smartphones, tablet computers, desktop/laptop computers, and similar. Features that mutually distinguish the remote devices 20 such as wearable devices 26, terminals 28, and terminals 30 are not contemplated to limit the present invention. Functionality of these devices 26-30 may overlap. Wearable devices 26 and terminals 28 collect data directly from users and may do so without the need for manual input by users. Wearable devices 26 and terminals 28 may allow for manual input by a user 32 (e.g., typing or selecting) of data. Terminals 30 may require some form of manual input by personnel 34 to enter data related to users 32.

The remote devices 20 may be configured to collect data.

The wide-area network 24 may include one or a combination of data networks, such as a local-area network, a wireless network, a cellular network, an intranet, a virtual private network (VPN), and the Internet.

The data system 22 may include one or more computers, which may be known as servers, configured with program code that is stored in memory and is executed by one or more processors to perform homomorphic calculations on data collected from the remote devices 20, as discussed in detail below.

The system may further include a key authority system 36 and analyst terminals 38.

The key authority system 36 stores one or more cryptographic keys, such as one or more private (secret) keys for a fully homomorphic asymmetric cryptographic scheme, such as a ring-learning with errors (RWLE) or NTRU homomorphic encryption scheme. The key authority system 36 includes one or more servers configured to store such private keys and restrict the use of the private keys to authorized users.

Each private key controlled by the key authority system 36 may correspond to a public key that is distributed to the remote devices 20. Data encrypted by the remote devices 20 could be decrypted by users with access to the respective private key, although this is not central to the present embodiment. According to the present embodiment, the results of homomorphic calculations performed on encrypted data may be decrypted by users with access to the respective private key. It is contemplated that a large number of remote devices 20 may share the same public key and thus form a large and continuous source of data for homomorphic calculations that do not require the decryption of the data. Rather, the private key may only be needed for the decryption of calculation results.

Any number of public-private key pairs may be used. It may be advantageous to segment devices 20 into different sets, according to device type or other factor, by providing such devices with different public keys. Different sets or types of devices 20 may be given different public keys based on other factors, such as the group/organization, device manufacturer, etc. Further, for a device 20 that collects multiple types of data, each type of data may be assigned to a different public key for encryption by that public key. Again, this may reduce exposure of user data. For sake of clarity, the examples discussed herein reference a single public-private key pair, but it should be noted that the present invention contemplates various public-private key pairs. Further, it is important to note that collaboration and computation using a set of data is limited to a set of encrypted data that is able to be decrypted by the same private key. Hence, to facilitate wide-ranging collaboration and computation, limiting the system to a single private key may be advantageous.

Analyst terminals 38 may include devices such as smartphones, tablet computers, desktop/laptop computers, and similar operable by analysts 40 such as administrators, researchers, and the like. Analyst terminals 38 may initiate homomorphic calculations performed at the data system 22 and may have the encrypted results of such calculations decrypted by the private key held by the key authority system 36. Plaintext results of the calculations may then be outputted at the analyst terminals 38 for further calculation and study.

The private key can be provided to decrypt calculation results in various ways, depending on specific requirements of various implementations according to the present invention. Encrypted results of calculations may be transmitted to the key authority system 36 for decryption at the key authority system 36, with the decrypted plaintext results (DR) 42 of the calculations being transmitted to one or more analyst terminals 38 for output via a secure channel 44, such as a secure subnetwork, a VPN operating through the wide-area network 24, or similar network that offers increased security. Additionally, or alternatively, such a secure channel 44 may be used to transmit the private key from the key authority system 36 to the analyst terminals 38 to decrypt calculation results at one or more analyst terminals 38. The secure channel 44 need not be limited to network communications. For example, analyst terminals 38 may be situated at physically secure locations, thereby offering a physical aspect to the secure channel 44, if the private key or encrypted data is to be transmitted over a network. Alternatively, the secure channel 44 may be mainly or exclusively physical and the private key or encrypted data can be copied onto physical key cards, memory sticks, or similar devices that can be used to manually convey the private key or encrypted data to the analyst terminals 38.

In operation, data may be continually collected by the remote devices 20, encrypted at the remote devices 20, and transmitted to the data system 22 as encrypted data (ED) 50. In general, any device transmitting data to the data system 22 may be configured to encrypt its data prior to transmission. The data system 22 may store the encrypted data 50 for as long as desired. At any time, an analyst terminal 38 may be used to select a set of data for analysis and to configure a calculation to be performed on the selected set of data. This information may be sent by the analyst terminal 38 to the data system 22 as a calculation command (CC) 52 that triggers the data system 22 to perform the calculation on the selected encrypted data, according to a homomorphic technique, without decrypting the data to obtain encrypted results 54. The encrypted results 54 of the calculation may then be transmitted to the analyst terminal 38. The analyst terminal 38 may then obtain decrypted results 42 using the secure channel 44 to communicate with the key authority system 36.

Advantageously, data may not be decrypted during the performance of calculations. User privacy may be improved and it is contemplated that more users may volunteer their data to be used in studies knowing that their data is better protected. In addition, opportunities for man-in-the-middle and other types of attacks may be mitigated due to the data and calculation results being transmitted in encrypted form and due to tight control of the private key.

In other applications, the remote devices 20 such as wearable devices 26, terminals 28, terminals 30, data system 22, terminals 38, remote devices 130 and other components may be specifically general purposes devices or devices made specific to a chosen application.

Figure 2:
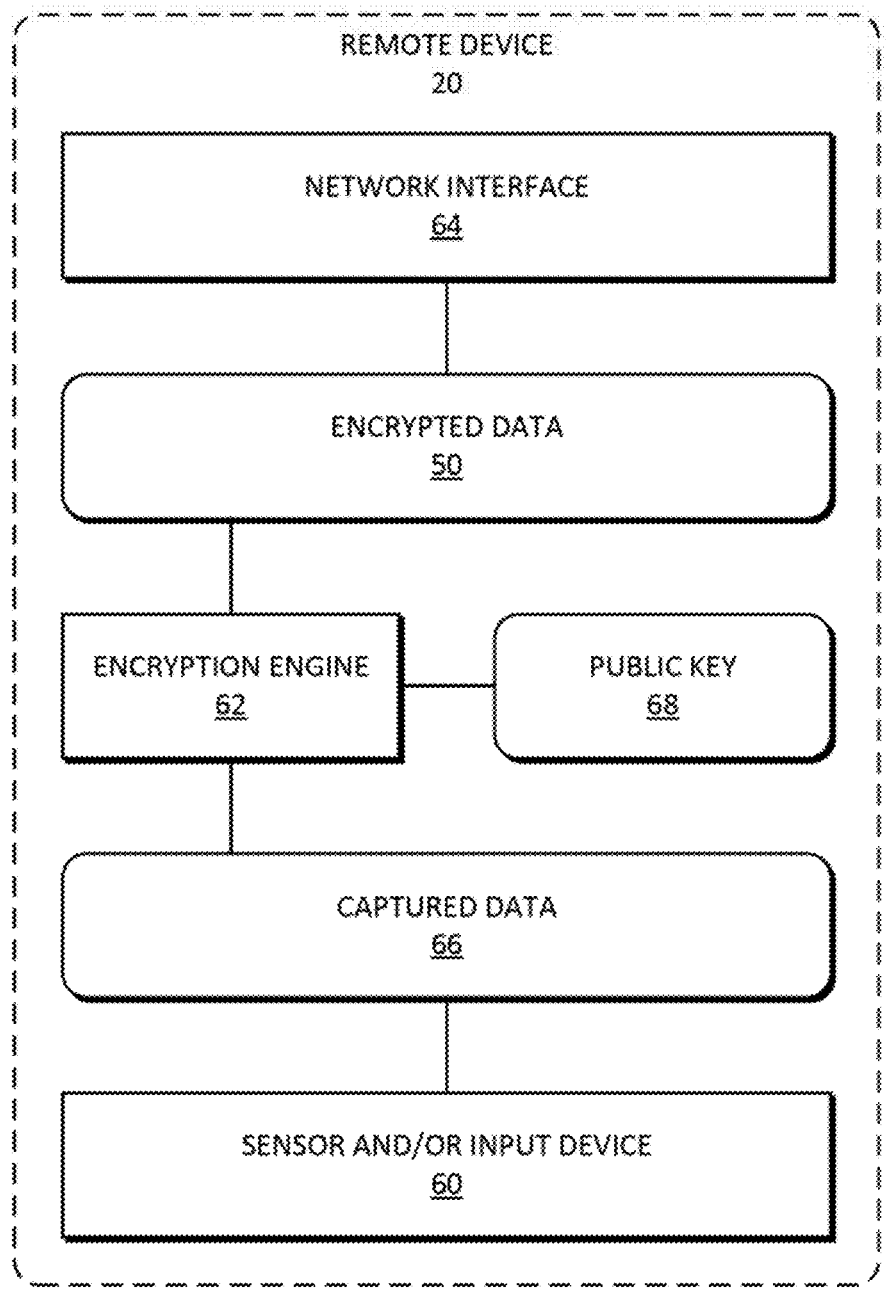
FIG. 2 is a diagram of a remote device according to an embodiment of the present invention.

FIG. 2 shows an example remote device 20. The remote device 20 may include a sensor 60 and/or input device, an encryption engine 62, and a network interface 64. The remote device 20 may further include memory (e.g., RAM, hard-drive, solid-state drive, etc.) for storing captured data 66, a public key 68, and encrypted data 50. The remote device 20 may also include a processor configured to execute the encryption engine 62 and control operations of the remote device 20.

The sensor and/or input device 60 may be configured to capture data of an individual. Example input devices include a keyboard or touchscreen, for manual entry of data. An input device may be used together with a sensor, such that the collected data includes manually inputted data as well as directly measured data. The type and nature of the data captured is not particularly limited.

The encryption engine 62 may be configured to apply the public key 68 to encrypt the captured data 66 to generate encrypted data 50. The encryption engine 62 may be configured to perform fully homomorphic encryption as discussed above.

The network interface 64 may be configured to communicate encrypted data 50 to the network 24 and specifically to the data system 22 (FIG. 1). After the encrypted data 50 has been transmitted to the data system 22, it may be deleted to save memory.

Figure 3:
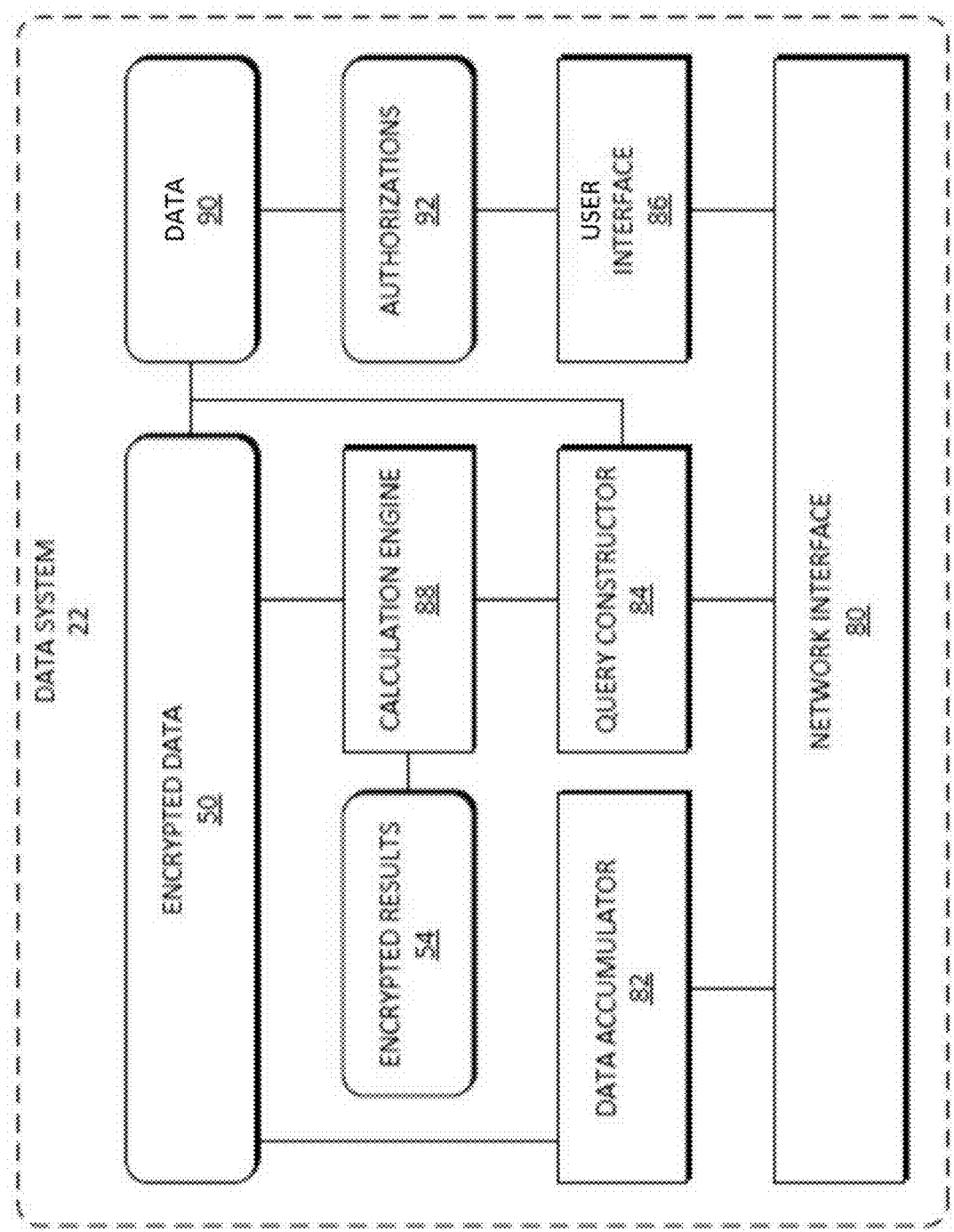
FIG. 3 is a diagram of a data system according to an embodiment of the present invention.

FIG. 3 shows an example of the data system 22. The data system 22 may include a network interface 80, a data accumulator 82, a query constructor 84, a user interface 86, and a calculation engine 88. The data system 22 may further include memory (e.g., RAM, hard-drive, solid-state drive, etc.) for storing encrypted data 50, encrypted calculation results (ER) 54, data 90, and authorizations 92. The data system 22 may also include a processor configured to execute the data accumulator 82, the query constructor 84, the user interface 86, and the calculation engine 88 and to control operations of the data system 22. It is noted that no encryption key need be stored at the data system 22, as the data system 22 performs its calculations on encrypted data.

The network interface 80 may be configured to receive data and commands from the network 24. The network interface 80 may be configured to receive encrypted data 50 and commands from the remote devices 20. The network interface 80 may be configured to receive calculation commands from analyst terminals 38.

The data accumulator 82 may be configured to control the capture of encrypted data 50 from the plurality of remote devices 20. The data accumulator 82 may be configured to periodically interrogate each remote device 20 for new encrypted data, receive such encrypted data in response, and store such encrypted data 50 in memory at the data system 22. The data accumulator 82 may be configured to reference the authorizations 92 as a condition for collecting data.

The query constructor 84 may be configured to receive calculation commands from analyst terminals 38. A calculation command triggers commencement of a calculation by the calculation engine 88. A calculation command may include parameters specifying a set of the encrypted data 50 on which to conduct a calculation as well as parameters specifying the nature of the calculation. The query constructor 84 may be configured to provide to the analyst terminals 38 a summary of the encrypted data 50 available for calculation. The query constructor 84 may be configured to reference the authorizations 92 as a condition for using elements of encrypted data 50 in calculations.

The user interface 86 may be configured to receive commands and data from remote devices 20, analyst terminals 38, or other devices and to output information about the encrypted data 50. Specifically, the user interface 86 may be configured to receive data 90 that is not necessarily encrypted. Data 90 may also include associations to the encrypted data 50, such that elements of encrypted data 50 may be linked to the data 90 that is considered useful for designing studies. For example, an association of data 90 to encrypted data 50 may include a unique identifier, such as a hash or serial number, of the user in both the encrypted data 50 and the data 90. It may be beneficial to include the unique identifier in the encrypted data 50 in plaintext form, such as via an unencrypted metadata field attached to the encrypted data 50, a file name, or an unencrypted database field in association with encrypted data 50 stored in a database.

The user interface 86 may be configured to receive commands to control authorizations 92 that are granted by users or other individuals to, for example, analysts at terminals 38. Authorizations 92 may include data indicative of the consent to collect and store encrypted data 50 and consent to make encrypted data 50 available to the calculation engine 88. In applications, authorizations 92 may include one or more many-to-many mappings that map users to data and further to individuals or organizations, such that each (or his/her legal representative) can give consent to provide any type of data to any individual or organization. Authorizations 92 may also include time windows for consent, such that consent is automatically withdrawn after expiry of a selected time.

The user interface 86 may include an authentication system, such as a username and password log-in authentication system, for verifying that users who modify data 90 and authorizations 92 are authorized to make such changes.

The calculation engine 88 may be configured to perform homomorphic calculations on encrypted data 50 according to received parameters defining the set of encrypted data 50 and the calculations to perform. The calculation engine 88 outputs encrypted results 54 that are transmitted via the network interface to the key authority system 36 or the analyst terminal 38. The calculation engine 88 can be configured to perform any suitable calculation in the encrypted domain.

Such calculations are contemplated to include addition, multiplication, discrete calculations, continuous calculations, comparisons using relational operations, combinations of such, and similar. Further, such calculations may be modeled as polynomial series. To achieve this, the calculation engine 88 may be configured as described below.

Figure 4:
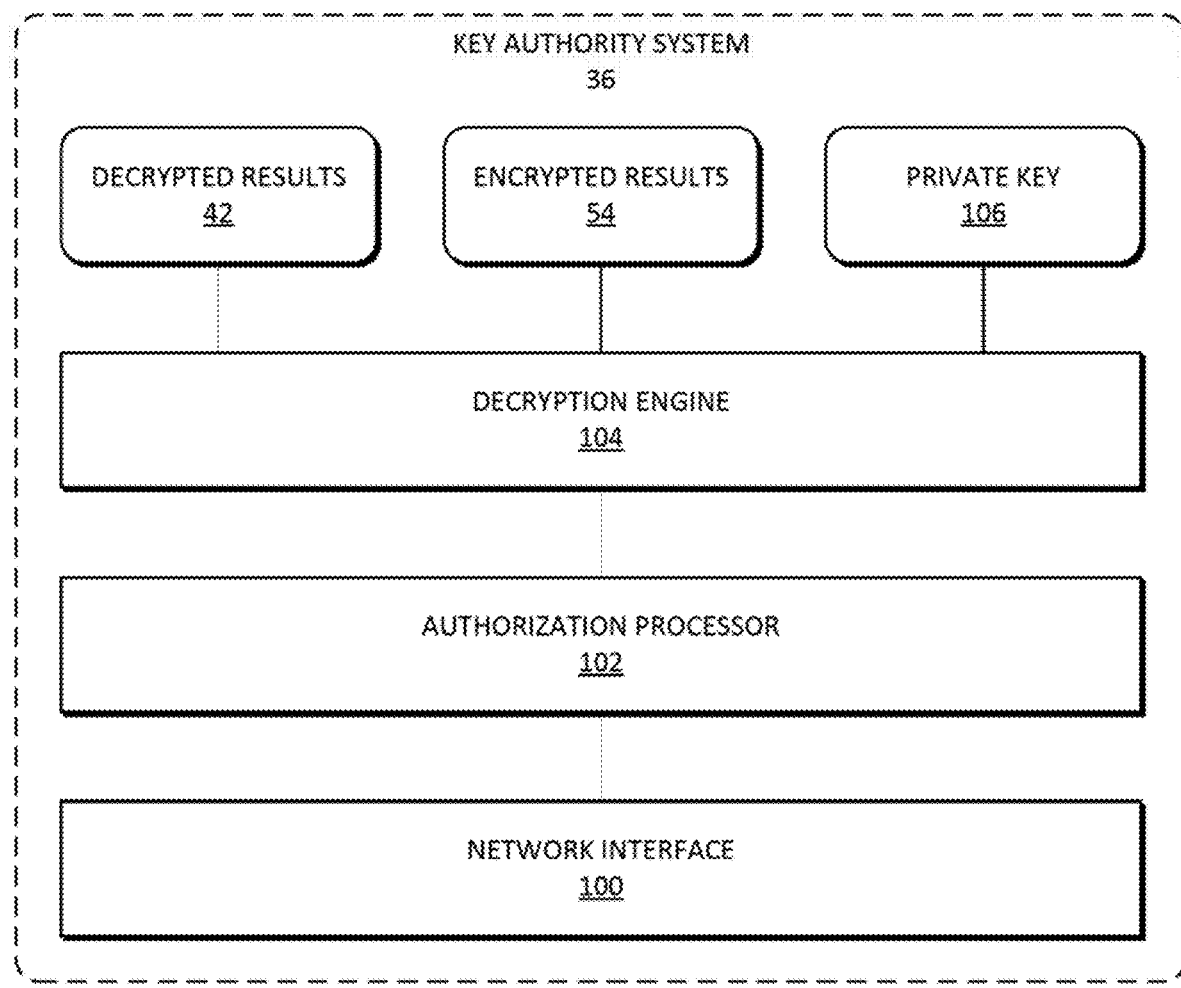
FIG. 4 is a diagram of a key authority system according to an embodiment of the present invention.

FIG. 4 shows an example key authority system 36. The key authority system 36 may include a network interface 100, an authorization processor 102, and a decryption engine 104. The key authority system 36 may further include memory (e.g., RAM, hard-drive, solid-state drive, etc.) for storing encrypted calculation results 54, a private key 106, and decrypted results 42. The private key 106 corresponds to the public key 68 (FIG. 2) stored in the remote devices 20. The key authority system 36 may also include a processor configured to execute the authorization processor 102 and the decryption engine 104, as well as to control operations of the key authority system 36.

The network interface 100 may be configured to receive encrypted results 54 from analyst terminals 38 via the secure channel 44 (FIG. 1). The network interface 100 may be further configured to transmit the decrypted results 42 to analyst terminals 38. Alternatively, or additionally, the network interface 100 may be configured to transmit the private key 106 to the analyst terminals 38 via the secure channel 44.

The authorization processor 102 may be configured to restrict access to the key authority system 36 to authorized users. The authorization processor 102 may include an authentication system, such as a username and password log-in authentication system or an electronic credential verification system, for verifying users who attempt to access the decrypted results 42 or the private key 106 or both.

The decryption engine 104 may be configured to apply the private key 106 to decrypt the encrypted calculation results 54 to generate the decrypted results 42. The decryption engine 104 may be configured to perform homomorphic decryption as discussed herein.

Figure 5:
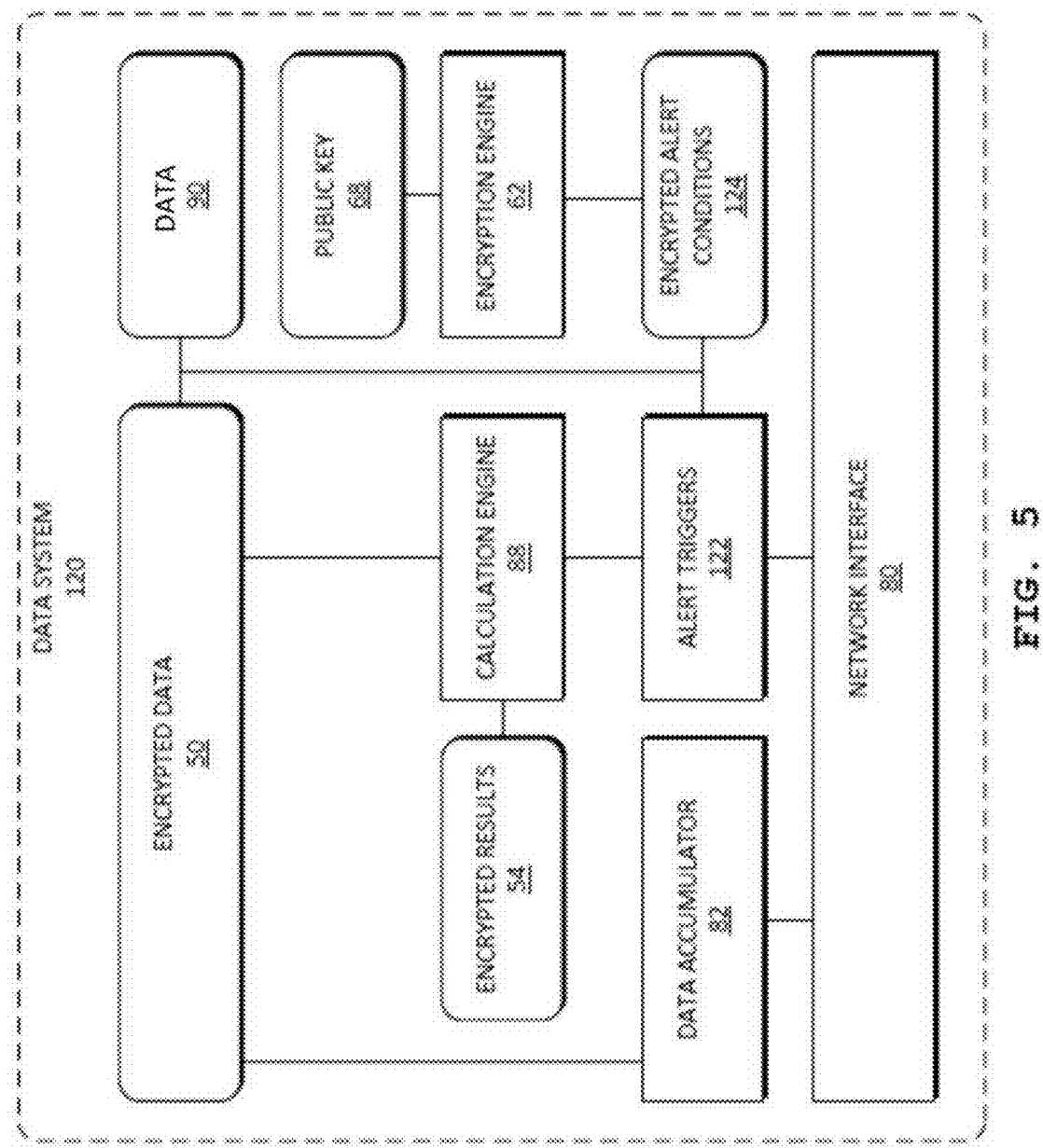
FIG. 5 is a diagram of another data system according to an embodiment of the present invention.

FIG. 5 shows a data system 120 according to an embodiment. The data system 120 may include components discussed herein, such as data system 22. The description for such components can be referenced with like reference numerals indicating like components. For sake of clarity, only differences will be discussed in detail. According to an embodiment, the data system 120 may replace the data system 22 in the system of FIG. 1.

The data system 120 may be configured to generate alerts based on calculations performed on encrypted data 50 received from remote devices 20. The data system 120 may transmit these alerts via the network 24 to remote devices 130 (FIG. 1) operated by professionals who may act on such alerts. It is contemplated that generated alerts remain in the encrypted domain. As such, alerts may be routed through the key authority system 36 for decryption prior to being transmitted to the relevant remote devices 130 in plaintext form. In such case, privacy may be enhanced by having the plaintext form of the alert be a general indication of the nature of the alert (e.g., a text alert) rather than specific numerical values, as it is contemplated that recipients of alerts may have background knowledge of the specific condition and perhaps knowledge of specific alert trigger values. Alternatively, remote devices 130 may be provided with the private key to decrypt received alerts.

The data system 120 may include alert triggers 122 executable by a processor and configurable by authorized users. The alert triggers 122 and the calculation engine 88 may perform comparisons between encrypted results 54 and encrypted alert conditions 124 stored in memory and configurable by authorized users. Encrypted alert conditions 124 may be initially received in unencrypted form via the network interface 80 before being encrypted by an encryption engine 62 using the same public key 68 that encrypts the data at the remote devices 20. Encrypted alert conditions 124 may be applied to data represented by the encrypted results 54 and alert triggers 122 issue alerts for data that meet the conditions. Such alerts may be configured to be transmitted via the network interface 80 and the network 24 to remote devices 130 of selected authorized users, such as professionals. Alerts may be communicated via the key authority system 36 for centralized decryption prior to being forwarded to the selected authorized users in plaintext form. Alternatively, the remote devices 130 may store the private key 106 and may be configured with a decryption engine 104 to decrypt the alerts. For example, a professional may set an alert condition 124 for a user, identified by data 90, using a equation homomorphically evaluated in the encrypted domain by the calculation engine 88 using data continuously collected by a wearable device 26. The encrypted alert condition 124 may be a particular maximum, minimum, or interval, if met or exceeded, causes the alert trigger 122 to send an electronic alert message to remote devices 130 operated by a professional who may be otherwise be unaware of the specific alert conditions. Advantageously, the specific evaluation and the values evaluated may remain in the encrypted domain, so as to improve privacy.

The alert triggers 122 may be evaluated on a periodic basis or upon detecting new encrypted data 50. The alert triggers 122 may store information concerning delivery of the alert, such as network addresses (e.g., email addresses, phone numbers, etc.) of the destination remote devices 130 that are to receive the alerts.

Various components of the data systems 22, 120, and specifically the calculation engine 88, may be implemented as one or more hardware devices. Such hardware devices may be configured to implement the computational techniques discussed herein using only hardware or by using hardware that executes program code. A suitable hardware device may be configured to implement the computational techniques discussed herein using, for example, Chinese Remainder Theorem (CRT), Number Theoretic Transform (NTT), one or more memory blocks, one or more memory interfaces, matrix multiplications, matrix additions, or a combination of such. One such suitable hardware device to achieve this is a Graphics Processing Unit (GPU). Other examples of suitable hardware device include a field-programmable gate array (FPGA) and an application-specific integrated circuit (ASIC).

Tests were conducted on a system constructed according to the present invention. FIG. 8 details the test system used. FIG. 9 summarizes performance results of the homomorphic operations for the present invention compared to Khedr, A., Gulak, G., and Vaikuntanathan, V. SHIELD: Scalable Homomorphic Implementation of Encrypted Data-Classifiers, Cryptology ePrint Archive, Report 2014/838, 2014 (http://eprint.iacr.org/2014/838.pdf) shown in FIG. 9 at "Khedr 2014"; Lauter, K., Lopez-Alt, A., and Naehrig, M. Private Computation on Encrypted Genomic Data. Tech. Rep, MSR-TR-2014-93, June 2014 shown in FIG. 9 at "Lauter 2014"; and LBos, J. W., Lauter, K., and Naehrig, M. Private predictive analysis on encrypted medical data, In *Journal of biomedical informatics*, Elsevier Inc., 2014, pp. 234-243 shown in FIG. 9 at "LBos 2014". The results reported for "Lauter 2014" are for larger parameters with larger circuit depth, as the circuit depth used to test the present invention is higher than in "Lauter 2014" with the chosen parameters. As can be seen, a CPU implementation of the present invention may achieve a 58 times speedup for a multiplication operation as compared to "LBos 2014". By additionally exploring the parallelizable properties of the present invention, a 104 times speedup may be achieved by distributing computations on GPU cores. This resulted in an overall 6085 times speedup for the multiplication operation compared to "LBos 2014" and a 286 times speedup compared to "Lauter 2014".

The present invention may be advantageously scalable across multiple GPU cards. Experiments were made using four GPU cards connected to the same computer to measure loss in performance due to cross-GPU communication. By partitioning large problems into small ones, computations can be scheduled among all four GPUs to obtain a speedup of 3.946 times, which indicates that communication overhead was reduced.

Additionally, according to an embodiment, the encryption scheme described herein may be used in privacy-preserving machine learning applications, in privacy-preserving data mining including privacy-preserving data clustering applications, and in general secure computations on financial or other confidential data. For example, the calculation engine 88 may be configured to perform homomorphic calculations related to privacy-preserving machine learning applications, in privacy-preserving data mining including privacy-preserving data clustering applications on encrypted data.

Numerous advantages may be apparent from the above description of the present invention. Concerning wearable and portable devices and the "Internet of Things" (IoT), the present invention can be used to encrypt all data measured by wearable and portable devices prior to uploading such data to the cloud. This can be very useful to help researchers conduct research on confidential data, in a manner that preserves privacy. As discussed, these devices can store public encryption keys produced by a centralized entity, which is also responsible for the control and distribution of private/secret keys to facilities where computation results/alerts are to be decrypted. Wearable/portable devices need only encrypt the captured data, and the modest processing power that is known in these kinds of devices is not a significant hindrance to implementation. Since performance of the encryption function is not necessarily time critical, embedded processors can encrypt measured data within seconds instead of milliseconds and still have acceptable performance.

The present invention may be embodied in other specific forms without departing from the spirit or essential characteristics thereof. Certain adaptations and modifications of the invention will be obvious to those skilled in the art. Therefore, the presently discussed embodiments are considered to be illustrative and not restrictive, the scope of the invention being indicated by the appended claims rather than the foregoing description and all changes which come within the meaning and range of equivalency of the claims are therefore intended to be embraced therein.

What is claimed is:

1. A method of processing a secure financial transaction, comprising:

receiving a transaction request to complete a financial transaction, with at least a portion of the request encrypted according to a homomorphic encryption scheme, and the transaction request comprising encrypted confidential cardholder data comprising a plurality of strings corresponding to a plurality of transaction and payment data in the encrypted confidential cardholder data, the plurality of transaction and payment data including an account number, other cardholder data, and transaction data;

retrieving one or more sets of encrypted comparison cardholder card data from a cardholder data database, each set of encrypted comparison cardholder card data encrypted according to a homomorphic encryption scheme and comprising a plurality of transaction and payment data corresponding to the plurality of transaction and payment data in the encrypted confidential cardholder data;

comparing the encrypted confidential cardholder data to each set of the encrypted comparison cardholder card data using one or more homomorphic operations comprising at least one multiplication operation on the plurality of strings collectively to determine which set of comparison cardholder card data matches the encrypted confidential cardholder data and validating the encrypted confidential cardholder data, wherein the one or more homomorphic operations combine to form an XNOR operation, wherein the XNOR operation is modelled as z=(1−x−y)(1−x−y);
retrieving the transaction data and comparing the transaction data using the one or more homomorphic operations to determine whether a transaction amount can be authorized;
generating an encrypted indicator indicating authorization or rejection of the request to complete the financial transaction based upon at least the validation of the encrypted confidential cardholder data; and
forwarding the encrypted indicator indicating authorization or rejection of the request to complete the financial transaction to a party seeking authorization to complete the financial transaction, wherein the encrypted confidential cardholder data is never decrypted during the method; and
wherein a portion of the request is compared to the set of encrypted comparison cardholder card data to reduce size of the set of encrypted comparison cardholder card data prior to comparing the encrypted confidential cardholder data.

2. The method of claim 1, wherein the homomorphic encryption scheme is a fully homomorphic encryption scheme or a somewhat homomorphic encryption scheme.

3. The method of claim 1, wherein the one or more homomorphic operations combine to form an XNOR operation.

4. The method of claim 1, wherein the request to complete the financial transaction is received by one or more of: a financial institution, a credit card company, a card issuer or a payment processor.

5. A non-transient computer-readable medium containing computer-readable instructions which when executed by a computer processor perform a method of:
receiving a transaction request to complete a financial transaction, with at least a portion of the request encrypted according to a homomorphic encryption scheme, and the transaction request comprising encrypted confidential cardholder data comprising a plurality of strings corresponding to a plurality of transaction and payment data in the encrypted confidential cardholder data, the plurality of transaction and payment data including an account number, other cardholder data, and transaction data;
retrieving one or more sets of encrypted comparison cardholder card data from a cardholder data database, each set of encrypted comparison cardholder card data encrypted according to a homomorphic encryption scheme and comprising a plurality of transaction and payment data corresponding to the plurality of transaction and payment data in the encrypted confidential cardholder data;
comparing the encrypted confidential cardholder data to each set of the encrypted comparison cardholder card data using one or more homomorphic operations comprising at least one multiplication operation on the plurality of strings collectively to determine which set of comparison cardholder card data matches the encrypted confidential cardholder data and validating the encrypted confidential cardholder data, wherein the one or more homomorphic operations combine to form an XNOR operation, wherein the XNOR operation is modelled as z=(1−x−y)(1−x−y);
retrieving the transaction data and comparing the transaction data using the one or more homomorphic operations to determine whether a transaction amount can be authorized;
generating an encrypted indicator indicating authorization or rejection of the request to complete the financial transaction based upon at least the validation of the encrypted confidential cardholder data; and
forwarding the encrypted indicator indicating authorization or rejection of the request to complete the financial transaction to a party seeking authorization to complete the financial transaction,
wherein the encrypted confidential cardholder data is never decrypted during the method; and
wherein a portion of the request is compared to the set of encrypted comparison cardholder card data to reduce size of the set of encrypted comparison cardholder card data prior to comparing the encrypted confidential cardholder data.

6. The computer-readable medium of claim 5, wherein the homomorphic encryption scheme is a fully homomorphic encryption scheme or a somewhat homomorphic encryption scheme.

7. The computer-readable medium of claim 5, wherein the request to complete the financial transaction is received by one or more of: a financial institution, a credit card company, a card issuer or a payment processor.

8. The method of claim 1, wherein determining whether the transaction amount can be authorized includes verifying that the encrypted confidential cardholder data is for a valid account.

9. The computer-readable medium of claim 5, wherein determining whether a transaction amount can be authorized includes verifying that the encrypted confidential cardholder data is for a valid account.

10. The method of claim 1, wherein the encrypted confidential cardholder data includes one or more of: a portion of the account number, the account number, an expiry date and a Card Verification Value (CVV) number.

11. The method of claim 1, wherein the other cardholder data includes one or more of: a bank name, a cardholder name, a Bank Identification Number (BIN) and a further portion of the account number.

12. The method of claim 1, wherein the transaction data includes one or more of: a transaction amount, a transaction date and a merchant identifier.

13. The method of claim 1, wherein the financial transaction is a credit card transaction or a debit card transaction or a stored-value card transaction.

14. The computer-readable medium of claim 5, wherein the encrypted confidential cardholder data includes one or more of: a portion of the account number, the account number, an expiry date and a Card Verification Value (CVV) number.

15. The computer-readable medium of claim 5, wherein the other cardholder data includes one or more of: a bank name, a cardholder name, a Bank Identification Number (BIN) and a further portion of the account number.

16. The computer-readable medium of claim 5, wherein the transaction data includes one or more of: a transaction amount, a transaction date and a merchant identifier.

17. The computer-readable medium of claim 5, wherein the financial transaction is a credit card transaction or a debit card transaction or a stored-value card transaction.

* * * * *